(12) United States Patent
Aoki et al.

(10) Patent No.: US 9,375,713 B2
(45) Date of Patent: Jun. 28, 2016

(54) LIQUID FEEDING SYSTEM FOR MICROCHIP, SAMPLE DETECTION DEVICE, AND LIQUID FEEDING METHOD FOR LIQUID FEEDING SYSTEM FOR MICROCHIP

(75) Inventors: Youichi Aoki, Hachioji (JP); Kusunoki Higashino, Osaka (JP); Naoki Hikage, Hachioji (JP)

(73) Assignee: KONICA MINOLTA, INC. (JP)

( * ) Notice: Subject to any disclaimer, the term of this patent is extended or adjusted under 35 U.S.C. 154(b) by 968 days.

(21) Appl. No.: 13/393,020

(22) PCT Filed: Sep. 3, 2010

(86) PCT No.: PCT/JP2010/065110
§ 371 (c)(1),
(2), (4) Date: Feb. 28, 2012

(87) PCT Pub. No.: WO2011/027851
PCT Pub. Date: Mar. 10, 2011

(65) Prior Publication Data
US 2012/0156800 A1    Jun. 21, 2012

(30) Foreign Application Priority Data

Sep. 7, 2009  (JP) ................................ 2009-205576
Sep. 25, 2009 (JP) ................................ 2009-220421

(51) Int. Cl.
*G01N 1/28* (2006.01)
*G01N 21/55* (2014.01)
(Continued)

(52) U.S. Cl.
CPC .......... *B01L 3/50273* (2013.01); *G01N 21/553* (2013.01); *G01N 21/648* (2013.01);
(Continued)

(58) Field of Classification Search
CPC ................. Y10T 436/2575; B01L 2400/0487;
B01L 3/50273; B01L 2300/0816; B01L 2300/0636; B01L 2300/0877; B01L 2200/0684; B01L 2200/143; G01N 33/54373; G01N 21/648; G01N 21/553; G01N 2035/106; G01N 2035/00158

See application file for complete search history.

(56) References Cited

U.S. PATENT DOCUMENTS

2004/0028559 A1    2/2004  Schuck
2006/0263263 A1*  11/2006  Shimizu ....................... 422/100
(Continued)

FOREIGN PATENT DOCUMENTS

JP    2006-90985 A    4/2006
JP    2006242912 A    9/2006
(Continued)

OTHER PUBLICATIONS

Office Action for Japanese Patent Application No. 2011-529951, dispatched Mar. 18, 2014, with English translation.
(Continued)

*Primary Examiner* — Christopher A Hixson
(74) *Attorney, Agent, or Firm* — Cantor Colburn LLP

(57) ABSTRACT

A liquid feeding system for a microchip performs: a first liquid feeding step in which a sample liquid in a sample liquid containing section is fed in the direction to a primary containing section via a reaction field; a second liquid feeding step in which, after the first liquid feeding step, the sample liquid is fed from the primary containing section in the direction to the reaction field; and a third liquid feeding step in which, after the second liquid feeding step, the feedings of the sample liquid from and to the reaction field and the primary containing section a rear side gas-liquid boundary face of the sample liquid in the first liquid feeding step and the front side and rear side gas-liquid boundary faces of the sample liquid in the second and third liquid feeding steps do not pass through the reaction field.

11 Claims, 12 Drawing Sheets

(51) Int. Cl.
- *G01N 21/64* (2006.01)
- *B01L 3/00* (2006.01)
- *G01N 21/552* (2014.01)
- *G01N 33/543* (2006.01)
- *G01N 35/00* (2006.01)
- *G01N 35/10* (2006.01)

(52) U.S. Cl.
 CPC ... *G01N33/54373* (2013.01); *B01L 2200/0684* (2013.01); *B01L 2200/143* (2013.01); *B01L 2300/0636* (2013.01); *B01L 2300/0816* (2013.01); *B01L 2300/0877* (2013.01); *G01N 2035/00158* (2013.01); *G01N 2035/106* (2013.01); *Y10T 436/2575* (2015.01)

(56) References Cited

U.S. PATENT DOCUMENTS

| | | | |
|---|---|---|---|
| 2007/0036679 A1* | 2/2007 | Munenaka | 422/68.1 |
| 2009/0038417 A1* | 2/2009 | Lee | 73/864.61 |

FOREIGN PATENT DOCUMENTS

| | | |
|---|---|---|
| JP | 2006-322896 A | 11/2006 |
| JP | 2007-38058 A | 2/2007 |
| JP | 2009-119386 A | 6/2009 |
| JP | 2009-122022 A | 6/2009 |

OTHER PUBLICATIONS

Miguel Abrantes et al: "Adaptation of a Surphace Plasmon Resonance Biosensor with Microfluidics for Use with Small Sample Volumes and Long Contact Times", Analytical Chemestry, vol. 73, No. 13, Jul. 1, 2001, pp. 2828-2835.
Extended European Search Report for Application No./Patent No. 10813798.5-1553/2477033, PCT/JP2010065110, dated Nov. 29, 2013.
International Search Report for International Application No. PCT/JP2010/065110 mailed Oct. 12, 2010 with English translation.
Written Opinion of the International Searching Authority for International Application No. PCT/JP2010/065110 dated Oct. 12, 2010 with English translation.
Miguel Abrantes et al: "Adaptation of a Surface Plasmon Resonance Biosensor with Microfluidics for Use with Small Sample vols. and Long Contact Times", Analytical Chemistry, vol. 73, No. 13, Jul. 1, 2001 —.
Office Action corresponding to European Patent Application No. 10813798.5-1553; Dated: Apr. 21, 2016.

* cited by examiner

LIQUID FEEDING SYSTEM FOR MICROCHIP, SAMPLE DETECTION DEVICE, AND LIQUID FEEDING METHOD FOR LIQUID FEEDING SYSTEM FOR MICROCHIP

CROSS REFERENCE TO RELATED APPLICATIONS

This is a U.S. national stage of application No. PCT/JP2010/065110, filed on 3 Sep. 2010. Priority under 35 U.S.C. §119(a) and 35 U.S.C. §365(b) is claimed from Japanese Application Nos. 2009-205576, filed 7 Sep. 2009, and 2009-220421, filed 25 Sep. 2009, the disclosure of which are also incorporated herein by reference.

FIELD OF THE INVENTION

The present invention relates to a microchip fluid transport system, a sample detection device, and transport method in a microchip fluid transport system, particularly to a microchip fluid transport system, a sample detection device, and transport method in a microchip fluid transport system used for the purpose of testing and analysis of biological material such as by gene amplification reaction, antigen-antibody reaction, or the like, testing and analysis of other chemical materials, chemical synthesis such as by organic synthesis, or the like of a target chemical compound, or the like.

BACKGROUND OF THE INVENTION

Conventionally, based on the principles of Surface Plasmon field enhanced Fluorescence Spectroscopy (SPFS), detection is being made, for example, of extremely small quantifies of analytes within an organism. The Surface Plasmon field enhanced Fluorescence Spectroscopy (SPFS) is a method of detecting extremely small quantities and/or extremely low concentrations of an analyte by, under conditions in which a laser light (excitation light) emitted from a light source undergoes attenuated total reflection (ATR) at the surface of a thin metal film, by causing the generation of density waves (surface plasmons) at the surface of the thin metal film and thereby enhancing the number of photons in the laser light (excitation light) emitted from a light source by several tens of times to several hundreds of times (the electric field enhancement effect of surface plasmons), and through this, efficiently exciting fluorescent materials in the vicinity of the thin metal film.

In recent years, developments are being made in surface plasmon field enhanced fluorescence spectroscope apparatuses based on this type of surface plasmon field enhanced fluorescence spectroscopy, and this technology has been disclosed, for example, in Patent Document 1.

Further, in Patent Document 1, in order to carry out measurement with a small quantity of the sample, by reciprocatingly feeding the analyte solution, the analyte solution is made to move reciprocatingly over the surface of a sensor onto which has been fixed an antibody that specifically bonds with the analyte in the analyte solution.

PRIOR ART DOCUMENTS

Patent Document

Patent Document 1: Unexamined Japanese Patent Application Publication No. 2006-90985.

SUMMARY OF THE INVENTION

Problems to be Solved by the Invention

When an analyte solution (hereinafter referred to as an analyte liquid) having an analyte therein is fed through a very thin flow path, it is easy for the flowing analyte liquid to go into the laminar flow state inside the very thin flow path, and in that case, only a part of the analyte liquid in the laminar flow state comes in contact with the antibody fixed onto the wall of the very thin flow path (the sensor surface of the reaction field).

In order to detect with good accuracy even with a small quantity of the analyte liquid, it is necessary to make the analyte liquid come in contact with the sensor surface uniformly, and in order to do that, it is possible to think of increasing the number of reciprocations of the analyte liquid.

However, if the analyte liquid is fed reciprocatingly, the wall surface of the very thin flow path becomes hydrophilic because of proteins contained in the analyte liquid getting adhered to that surface. Because of this, as in Patent Document 1, in the case in which the analyte liquid is made to move reciprocatingly in a condition in which the gas-liquid interface which is the boundary surface between the analyte liquid and air inside the very thin flow path is moved, air bubbles may be generated due the phenomenon of the analyte liquid completely overtaking air at the air-liquid interface.

When air bubbles are generated, the air bubbles themselves act as a damper causing deterioration of responsivity of liquid feeding, or the passage of liquid becomes poor due to the effect of air bubbles near the injection inlet connecting the pipette with the flow path. Further, if the reaction field is covered by air bubbles, no reaction will occur because the analyte liquid does not come into contact with that part. Because of such phenomena, the amount of reaction of the analyte solution in the reaction field decreases, and as a result, it will not become possible to detect with good accuracy.

A first problem to be solved by the present invention, considering the abovementioned problem, is to provide a liquid feeding system for a microchip and a method thereof, which, even if the sample is small, prevents reduction of the amount of reaction in the reaction field, and thus makes it possible to detect an analyte with good accuracy.

Further, on the other hand, in the abovementioned liquid feeding system for a microchip of the reciprocating liquid feeding type (hereinafter referred to merely as "reciprocating type"), since the reciprocating liquid feeding pump is made to change the liquid feeding direction at prescribed units of time, even if the direction changing accuracy of the reciprocating liquid feeding pump is good, particularly when a large number of air bubbles are present inside the flow path on the outlet side near the reciprocating liquid feeding pump, this air becomes a damper and it takes time for stopping the analyte liquid and to change the direction of liquid feeding, and a shift will occur in the timing of changing the direction of feeding the liquid and starting the liquid feeding again. In particular, as the number of reciprocations increases, shifts in the reciprocating position of the analyte liquid gradually get accumulated, and there were cases in which the analyte liquid shifted from the reaction field.

If the reciprocating position shifts from the reaction field in this manner, it does not become possible to capture the desired analyte in the reaction field.

A second problem to be solved by the present invention is the purpose of providing a sample detection device using a liquid feeding system for a microchip and a method thereof, wherein it is possible to reciprocatingly feed an analyte liquid to the reaction field, and hence make it possible to retain the desired analyte in the reaction field and to detect the analyte with high accuracy.

Means for Solving the Problems

The above purposes are satisfied by the inventions described below.
1. A liquid feeding system for a microchip comprising;
a flow path having a reaction field in which is fixed an antibody that reacts specifically with an antigen in an analyte liquid;
an analyte liquid storage section connected to one end side of said flow path;
a primary storage section connected to the other end side of said flow path;
applying driving force via a gas to the analyte liquid in said analyte liquid storage section; and
a control section that controls the drive of said pump;
wherein said control section;
not only carries out a first liquid feeding step of feeding the analyte liquid of said analyte liquid storage section via said reaction field in the direction of said primary storage section, a second liquid feeding step of feeding the analyte liquid after said first liquid feeding step from said primary storage section in the direction of said reaction field, and a third liquid feeding step of repeating the feeding of the analyte liquid after said second liquid feeding step from said reaction field in the direction of said primary storage section and the feeding of the analyte liquid from said primary storage section in the direction of said reaction field, but also carries out control of said pump so that a rear gas-liquid interface of the analyte liquid in said first liquid feeding step and the front gas-liquid interface of the analyte liquid in said second liquid feeding step do not pass beyond said reaction field.
2. A liquid feeding method for a liquid feeding system for a microchip comprising;
a flow path having a reaction field in which is fixed an antibody that reacts specifically with an antigen in an analyte liquid;
an analyte liquid storage section connected to one end side of said flow path;
a primary storage section connected to the other end side of said flow path; and
a pump that reciprocatingly feeds the analyte liquid with respect to said reaction field by applying driving force via a gas to the analyte liquid in said analyte liquid storage section;
wherein said liquid feeding method comprises;
a first liquid feeding step of feeding the analyte liquid of said analyte liquid storage section via said reaction field in the direction of said primary storage section;
a second liquid feeding step of feeding the analyte liquid after said first liquid feeding step from said primary storage section in the direction of said reaction field; and
a third liquid feeding step of repeating the feeding of the analyte liquid after said second liquid feeding step from said reaction field in the direction of said primary storage section and the feeding of the analyte liquid from said primary storage section in the direction of said reaction field, and characterized in that the rear gas-liquid interface of the analyte liquid in said first liquid feeding step and the front gas-liquid interface of the analyte liquid in said second liquid feeding step do not pass beyond said reaction field.

Effect of the Invention

By making the rear gas-liquid interface of the analyte liquid in said first liquid feeding step and the front gas-liquid interface of the analyte liquid in said second liquid feeding step not pass beyond said reaction field, generation of air bubbles is prevented, and it becomes possible to prevent the effects of those air bubbles, and consequently, it becomes possible to provide a liquid feeding system for a microchip and a liquid feeding method thereof that, even with a small quantity of the analyte, makes it possible to detect with good accuracy.

BRIEF DESCRIPTION OF THE DRAWINGS

FIG. 7a shows the amount of reaction versus the number of reciprocations, and FIG. 7b shows the amount of reaction versus the liquid feeding time.

FIG. 9a is a state diagram before the analyte liquid is fed by the reciprocating liquid feeding pump, FIG. 9b is a state diagram during the period in which the analyte liquid is being fed by the reciprocating liquid feeding pump, FIG. 9c is a state diagram when the analyte liquid is fed by the reciprocating liquid feeding pump and the first liquid position checking sensor has detected the analyte liquid, and FIG. 9d is a state diagram when the liquid feeding direction of the reciprocating liquid feeding pump has been switched to the opposite direction and the second liquid position checking sensor has detected the analyte liquid.

FIG. 11a is a state diagram before actuating the variable volume section, FIG. 11b is a state diagram immediately before actuating the variable volume section, FIG. 11c is a state diagram when the variable volume section is actuated and also the first liquid position checking sensor has detected the analyte liquid, and FIG. 11d is a state diagram when the liquid feeding direction of the reciprocating liquid feeding pump has been switched to the opposite direction and the second liquid position checking sensor has detected the analyte liquid.

DETAILED DESCRIPTION OF THE PREFERRED EMBODIMENTS

Although the present invention will be described here based on the best modes for carrying out the invention, the present invention is not restricted by these best modes.

Figure 1:
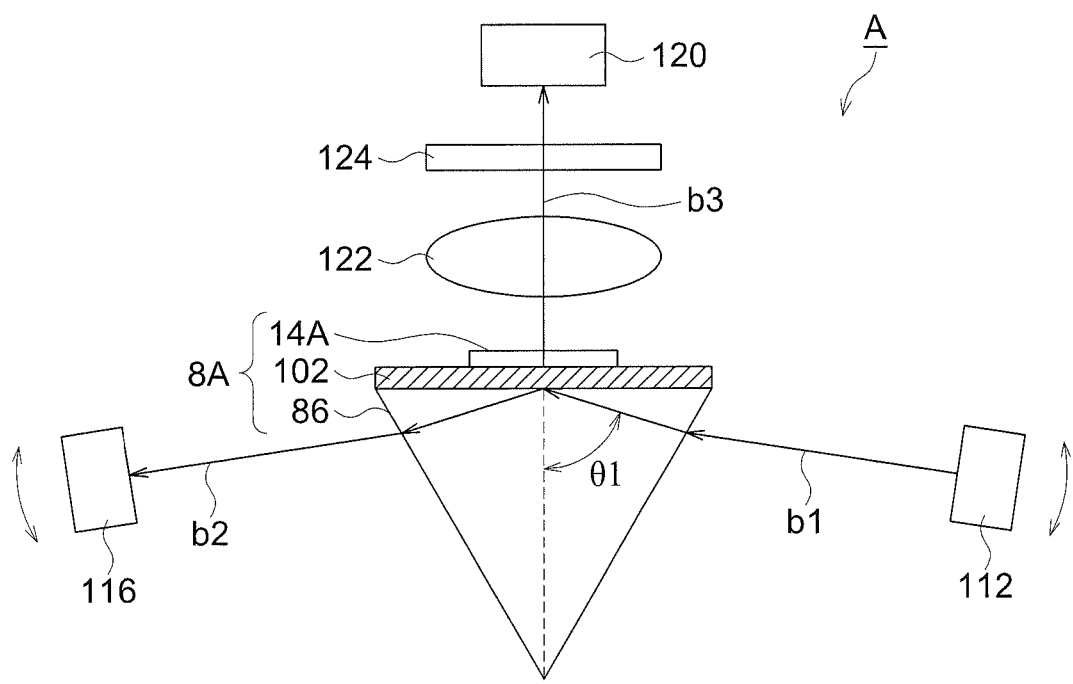
FIG. 1 is an outline diagram of a surface plasmon field enhanced fluorescence spectroscopy apparatus using a liquid feeding system for a microchip according to a first preferred embodiment.
Figure 2A:
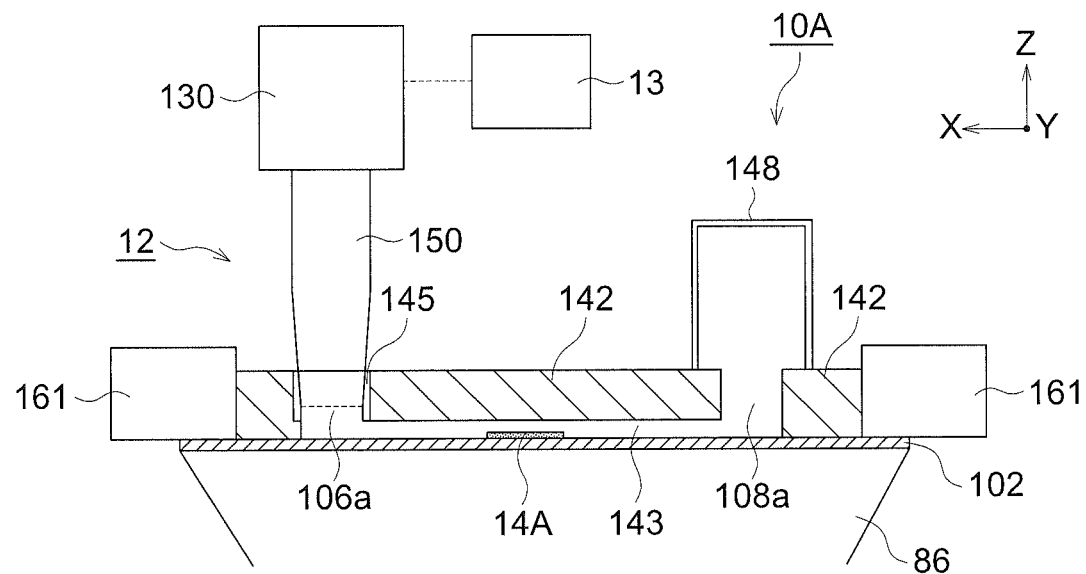
FIG. 2a is a cross-sectional view diagram near the microchip 12.
Figure 2B:
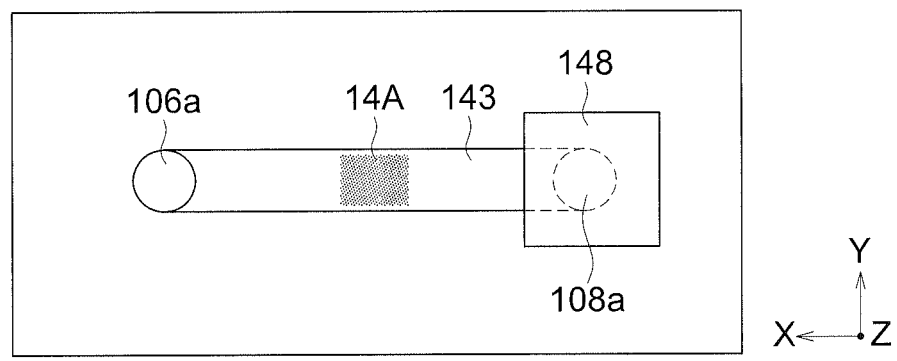
FIG. 2b is a top view diagram of a part thereof.

FIG. 1 and FIGS. 2a and 2b are outline diagrams of a surface plasmon field enhanced fluorescence spectroscopy apparatus using a liquid feeding system for a microchip according to a first preferred embodiment.

A surface plasmon field enhanced fluorescence spectroscopy apparatus is an apparatus that highly accurately detects the fluorescent light emitted by a fluorescent material which has been excited by generating density waves (surface plasmon) at the surface of a thin metal film by illuminating said thin metal film by an excitation light, and thereby increasing the detection sensitivity

[Surface Plasmon Field Enhanced Fluorescence Spectroscopy Apparatus A, and Analyte Detection Method]

A surface plasmon field enhanced fluorescence spectroscopy apparatus A of the present invention is provided with, as is shown in FIG. 1, a chip structure member 8A having, firstly a thin metal film 102, a reaction field 14A formed on the surface on one side of the thin metal film 102, and a dielectric member 86 formed on the surface on the other side.

Further, on the side of the dielectric member 86 of the chip structure member 8A is provided a light source 112 that emits an exciting light b1 which is incident into the dielectric member 86 and is irradiated towards the thin metal film 102, and also a light receiving section 116 is provided that receives the reflected light b2 which is emitted from the light source 112 and is reflected from the thin metal film 102.

Here, the excitation light b1 emitted from the light source 112 is preferably a laser light, and gas or solid state laser light with wavelengths of 200 to 1000 nm, or semiconductor laser light with wavelengths of 385 to 800 nm is very suitable.

On the other hand, on the side of the reaction field 14A of the chip structure member 8A is provided a light detection section 120 that receives the fluorescence light b3 generated in the reaction field 14A.

As a light detection section 120, it is preferable to use an ultra high sensitivity photomultiplier tube, or a CCD image sensor that can measure multiple points.

Further, between the reaction field 14A of the chip structure member 8A and the light detection section 120 are provided a light focusing member 122 for efficiently focusing the light, and a filter 124 constituted so that the fluorescence light b3 is transmitted selectively while reducing the passage of light with wavelengths other than that of the fluorescence light b3 in the entire light As the light focusing member 122 it is possible to use any light focusing system as long as the purpose of efficiently focusing the fluorescence light signal on the light detecting section 120 is achieved. As a simple light focusing system, it is also possible to adapt an objective lens used in microscopes and sold in the market. A magnification of 10 to 100 times is preferable as the magnification of the objective lens.

Further, as the filter 124, it is possible to use an optical filter, a cutoff filter, or the like. As an optical filter, it is possible to use a neutral density (ND) filter, a diaphragm lens, or the like. Further, as a cutoff lens, it is possible to use, for example, an interference filter; color filter, or the like, which are filters that remove various types of noise lights such as, external light (illumination light from outside the apparatus), excitation light (the transmission component of the excitation light), stray light (the excitation light components scattered from various locations), light scattered by the plasmon (the scattered light generated due to the effect of structural members or adhered material on the surface of the plasmon excitation sensor with the excitation light as the light source), the auto-fluorescence of the enzyme fluorescent substrate, or the like.

Further, in the method for detecting an analyte using such a surface plasmon field enhanced fluorescence spectroscopy apparatus A, on the surface of the thin metal film 102 that comes into contact with the reaction field 14A is provided an SAM film (also called a Self-Assembled Monolayer film), or a polymer substance film, with a primary antibody bound thereto. A primary antibody is bonded only on one surface of the SAM film or polymer substance film, and the other surface of the SAM film or polymer substance film is fixed directly or indirectly onto the surface of the thin metal film 102. As a SAM film, it is possible to use, for example, a film made of a substituted aliphatic thiol such as HOOC—(CH2) 11-SH, or the like, and as a polymer material, it is possible to use, for example, polyethylene glycol, or MPC polymer, or the like. These can be prepared either at the time of using, or else it is possible to use a substrate to which they have been bonded beforehand. Further, it is also possible to fix directly on a substrate a polymer provided with a radical reactive to the primary antibody (or a functional radical that can be converted into a reactive group), and the primary antibody can be fixed thereupon. At the time of bonding the antibody or polymer using various types of reactive groups, an amidation condensation reaction after passing through conversion to succinimidyl, or addition reaction after passing through conversion to maleimide, or the like are common.

From the first liquid feeding step to the fourth liquid feeding step described later, a solution that includes the antigen of the analyte obtained as the target material (hereinafter called the analyte liquid) and a reagent liquid that includes a secondary antibody are fed to the reaction field configured in this manner. It is possible to capture the antigen by a fixed primary antibody. The captured antigen is labeled by causing a reagent liquid that includes a secondary antibody that has been labeled by a fluorescent material to act further on this. Further, it is also possible to make the primary antibody act after first making the antigen and the secondary antibody react In the "detection step" of detecting an analyte labeled with a fluorescent material, an excitation light b1 is emitted from a light source 112 towards the dielectric member 86 for the reaction field where the analyte has been captured, because this excitation light b1 is made to be incident on the thin metal film 102 at a specific angle of incidence (the resonance angle θ1), density waves (surface plasmons) are generated in the thin metal film 102.

Further, at the time that density waves (surface plasmons) are generated on the surface of the thin metal film 102, since the excitation light b1 and the electron vibrations in the thin metal film 102 get coupled, and since the signal of the reflected light b2 from the thin metal film 102 changes (the amount of light decreases), it is sufficient to find out the locations where the signal of the thin metal film reflected light b2 received by the light receiving section 116 changes (the amount of light decreases).

Next, due to these density waves (surface plasmons), the fluorescent material generated in the reaction field 14A on this thin metal film 102 is efficiently excited, and because of this the amount of fluorescence light b3 emitted by the fluorescent material is increased, and by detecting this fluorescence light b3 by the light detection section 120 via a light focusing member 122 and a filter 124, it is possible to detect very small amounts and/or an extremely low concentration of the analyte.

Further, the material of the thin metal film 102 of the chip structure member 8A is preferably composed of at least one type of metal selected from a group comprising gold, silver, aluminum, copper, and platinum, more preferably from gold, and still more preferably from an alloy of these metals.

Such metals are very suitable as the thin metal film 102, because they are stable against oxidization, and also because the electric field enhancement for density waves (surface plasmons) becomes high.

Further, as a method for forming the thin metal film 102, it is possible to use, for example, sputtering, vacuum evaporation (resistance heating evaporation method, electron beam evaporation method, or the like), electrolytic plating, non-electrolytic plating, or the like. Among these, the sputtering method and the evaporation methods are preferable because it is easy to adjust the thin film forming conditions.

Further, it is preferable that the thickness of the thin metal film is in the range of, gold: 5 to 500 nm, silver: 5 to 500 nm, aluminum: 5 to 500 nm, copper: 5 to 500 nm, platinum: 5 to 500 nm, and their alloys: 5 to 500 nm.

From the point of view of the electric field enhancement effect, it is preferable that the thickness is in the range of gold: 20 to 70 nm, silver: 20 to 70 nm, aluminum: 10 to 50 nm, copper 20 to 70 nm, platinum: 20 to 70 nm, and their alloys: 10 to 70 nm.

The thickness of the thin metal film 102 being within the above range is suitable because it is easy for the density waves (surface plasmons) to be generated. Further, if the thin metal film 102 is one having such a thickness, the size (vertical× horizontal) is not particularly restricted.

Further, as the dielectric member 86, it is possible to use a prism with a high refractive index of about 60. As the material, it is possible to use various types of optically transparent inorganic materials, natural polymers, or synthetic polymers, and from the point of view of chemical stability, manufacturing stability, and optical transparency, it is preferable to include silicon dioxide ($SiO_2$) or titanium dioxide ($TiO_2$).

In addition, such a surface plasmon field enhanced fluorescence spectroscopy apparatus A is provided with an angle varying section (not shown in the figure) for adjusting the optimum angle (resonance angle $\theta 1$) of surface plasmon resonance by the excitation light b1 incident on the thin metal film 102 from the light source 112.

Here, the angle varying section (not shown in the figure) is controlled by the control section 13, and in order to obtain the attenuated total reflection (ATR) condition in the resonance angle scanning step using the servomotor of the angle varying section, the light receiving section 116 and the light source 112 are synchronized and rotated with the illumination area as the center, and the angle can be changed in the range of 45 to 85°. Further, it is desirable that the resolution is 0.01° or more.

FIG. 2a is a cross-sectional view diagram near the microchip 12, and FIG. 2b is a top view diagram of a part thereof. In FIG. 2a, a substrate 142 is attached as a cover plate to the chip structure member 8A shown in FIG. 1. At least in the part of the substrate near the reaction field 14A it is necessary to use a material that transmits the fluorescence light b3, and quartz is being used as the substrate in the present preferred embodiment. Further, a very fine flow path 143 has been formed in the substrate 142 which is a quartz substrate, and in the condition shown in FIG. 2a, the bottom surface of the very fine flow path 143 is constituted by the dielectric member 86 on whose surface the thin metal film 102 has been formed.

The substrate 142 whose periphery is supported by fixing brackets 161 is fixed to the dielectric member 86 without any gaps in between.

The aforementioned reaction field 14A is provided in a path of the very fine flow paths 143. An inlet hole 106a is provided at one end section of the very fine flow path 143, and an outlet hole 108a is provided at the other end section of the very fine flow path 143. Further, a connection section 145 is provided on the side of the inlet hole 106a.

The connection section 145 can be connected to a pipette 150 functioning as an "analyte liquid storage section". The connection section 145 is constituted from an elastic material, and functions as a sealing member at the time of inserting the pipette 150. Beyond the outlet hole 108a at the other end is provided a mixing section 148 that functions as a "primary storage section". Further, in the top part of the mixing section 148 are provided very fine air holes not shown in the figure.

The width (length along the Y direction) of the very fine flow path 143 is taken as 1 mm to 3 mm, height (along the Z direction) as 50 μm to 500 μm, the width of the reaction field 14A is equivalent to the width of the very fine flow path 143, and the length is taken as 1 mm to 3 mm, but these dimensions need not necessarily be limited to these values. Further, the sizes of the inlet hole 106a and the outlet hole 108a at the two ends of the very fine flow path 143 are φ1 mm to φ3 mm equivalent to the width of the very fine flow path 143. The tip of the pipette 150 has almost the same shape as the inlet hole 106a, and the base part thereof has a cylindrical shape with a slightly larger diameter at the base. The mixing section 148 has a larger cross-sectional shape than the outlet hole 108a, and, for example, has a 2 to 4 mm roughly square shape. Further, although a roughly square cross-sectional shape has been shown in FIG. 2b, the cross-sectional shape can also be a circular one.

In FIG. 2a, a condition is shown in which a pipette 150 has been inserted. As is clear from this figure, in the inserted condition, the pipette 150 and the mixing section 148 are both above a horizontal plane passing through the very fine flow path 143, and have been provided at a higher position than the height of the upper wall inside surface of the very fine flow path 143 at the reaction field 14A. Further; although an example has been shown in which the mixing section 148 has been fixed to the microchip 12, it is also possible to have a configuration in which it can be detached similar to the pipette 150. Further, it is sufficient if the pipette 150 has rigidity so that it does not get deformed with respect to the changes in the internal pressure caused by the drive of the reciprocating liquid feeding pump 130 but there is almost no change in its volume. In the present preferred embodiment, polypropylene has been used as the material. Further, it can be attached and detached freely via the connection section 145, and it is possible to easily dispose of it together with the supplied analyte liquid and the pipette 150.

The control section 13, is provided with a CPU and memory, and controls the reciprocating liquid feeding pump 130 and the like by executing a program stored in the memory. The reciprocating liquid feeding pump 130 is, for example, a syringe pump, and it is possible to carry out reciprocating liquid feeding by ejecting or sucking in a prescribed quantity of liquid.

Further, in the present patent specification, conveying the liquid inside the pipette 150 in the forward direction which is the direction from the reaction field 14A towards the mixing section 148 (in the direction from the inlet hole 106a towards the outlet hole 108a in the very fine flow path 143 in FIG. 2a) is called "ejecting", and conveying in the opposite direction which is the direction from the mixing section 148 towards the reaction field 14A is called "sucking in". Further, feeding the liquid without differentiating between ejecting and sucking in is called "liquid feeding". Further, although in the preferred embodiment the ejecting and sucking in of liquid are being carried out with a single pump, it is also possible to provide pumps for ejecting respectively at the two ends of the very fine flow path 143 thereby carrying out liquid flow in both directions.

Because of controlling the reciprocating liquid feeding pump 130 by the control section 13, it is possible to make a liquid such as an analyte liquid stored inside the pipette 150 be ejected into or sucked in from the inside of the microchip 12. In this manner, a reagent that includes a fluorescent material labeled secondary antibody or an analyte liquid having an analyte is fed by the reciprocating liquid feeding pump 130.

An analyte can be blood, blood serum, blood plasma, urine, mucous, saliva, feces, body cavity fluid (spinal fluid, fluid in the abdomen, pleural effusion, or the like). The analyte in included in the analyte can be, for example, nucleic acid (single chain or double chain DNA, RNA, polynucleotide, oligo nucleotide, PNA (peptide nucleic acid), or the like, or, nucleoside, nucleotide, or their modified molecules, proteins (polypeptide, oligo peptide, or the like), amino acids (including modified amino acid, saccharides (oligo saccharide, poly saccharide, sugar chain, or the like), fats, or their modified molecules, or their composites, and more specifically, carcino embryonic antigens or tumor markers such as AFP ($\alpha$-fetoprotein), signal transmission materials, hormones, or the like, and are not particularly restricted.

In addition, as a fluorescent material, it is possible to use any material that emits fluorescence light b3 upon being excited by either illumination with a prescribed excitation light b1, or using the electric field effect, and is not particularly restricted. Further, the fluorescence light b3 in the present patent specification includes even various types light emissions such as phosphorescence.

[Control Flow of Analyte Capturing and Detection]

Figure 3:
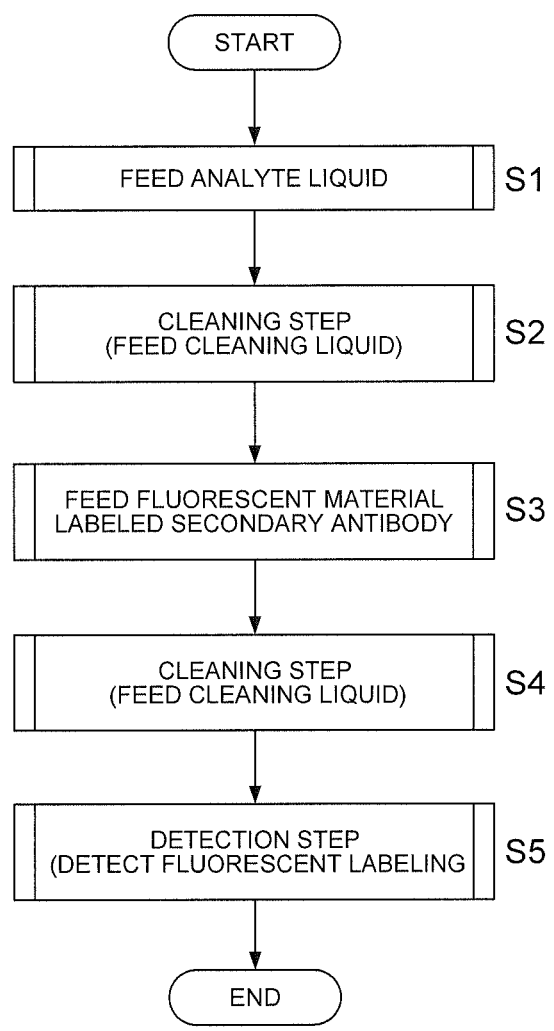
FIG. 3 is a diagram showing the control flow that is executed by the control section 13.

FIG. 3 is a diagram showing the control flow that is executed by the control section 13. In step S1, the analyte liquid that is fed is an analyte dissolved in a solvent. Details related to liquid feeding are explained based on FIG. 4 and FIGS. 5a through 5d.

Figure 4:
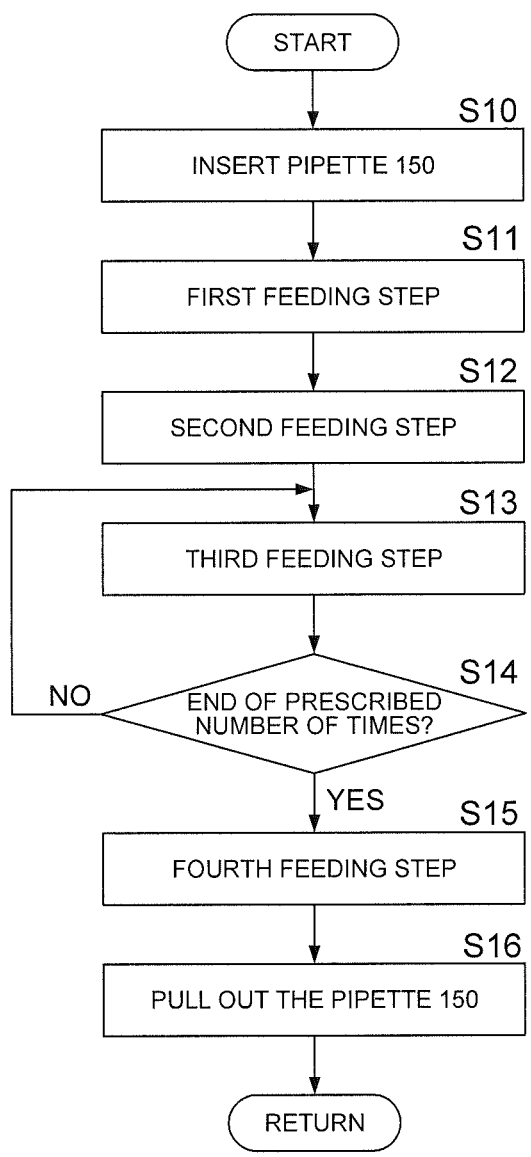
FIG. 4 is a flow diagram of the subroutine related to Step S1 (or Step S2, S3, or S4) of FIG. 3, FIGS. 5a through 5d are schematic diagrams for explaining the flow of liquid feeding in an example of implementation.

FIG. 4 is a flow diagram of the subroutine related to Step S1 of FIG. 3. In step S10 of FIG. 4, a pipette 150 into which a prescribed quantity of an analyte liquid has been injected is inserted into the connection section 145 of the microchip 12. FIG. 5a through FIG. 5d are schematic diagrams for explaining the flow of liquid feeding. In these liquid feedings, by controlling the reciprocating liquid feeding pump 130 the control section 13 applies a driving force to the analyte liquid Lq via a gas.

Figure 5A:
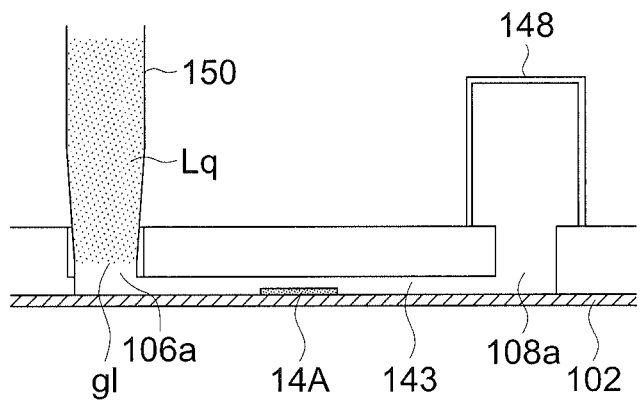

FIG. 5a is a diagram corresponding to step S10, and this figure shows the initial condition in which a pipette 150 into which a prescribed quantity of an analyte liquid has been injected has been inserted. Further, in the preferred embodiment shown in FIG. 5a through FIG. 5d, the injected amount m1 of analyte liquid Lq is taken as 200 μl, and the volume m2 of the very fine flow path 143 is taken as 10 μl.

In the first liquid feeding step (step S11) of FIG. 4, a liquid feeding amount m3 of the analyte liquid Lq is ejected. Because of ejecting, since the analyte liquid passes over the top surface of the reaction field 14A provided inside the very fine flow path 143, the antigen included in the analyte liquid Lq specifically reacts with and is captured by the primary antibody fixed to the reaction field 14A.

Figure 5B:
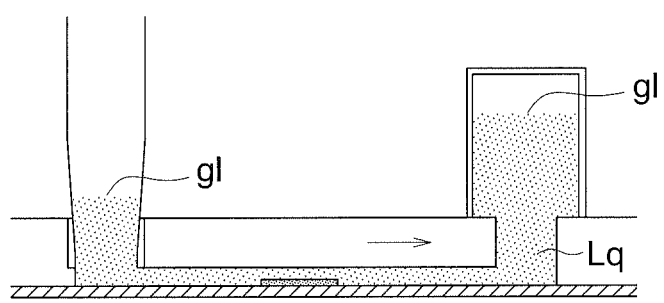

FIG. 5b is a figure showing the state immediately after the first liquid transport step of ejecting a liquid feeding amount m3 of the analyte liquid Lq. The liquid feeding amount m3 in the first liquid feeding step from the state of FIG. 5a to the state of FIG. 5b is being taken as 195 μl. By making this liquid feeding amount m3, (1) in the first liquid feeding step the rear gas-liquid interface gl in the direction of feeding of the analyte liquid Lq does not pass the reaction field 14A. (2) Also, since the construction is such that the inlet hole 106a is positioned so as to be higher than the height of the inner surface of the top wall of the very fine flow path 143 in the reaction field 14A, the rear gas-liquid interface gl continues to be positioned higher than the height of the inner surface of the top wall of the very fine flow path 143 in the reaction field 14A. Further, (3) it is possible to make a sufficient amount of the analyte liquid pass over the top surface of the reaction field 14A, and in addition, (4) a sufficient amount, 185 μl, of the analyte liquid Lq will be stored temporarily inside the mixing section 148.

[Effect of Providing the Mixing Section 148]

The effect of providing the mixing section 148 is explained here. As a comparison example, a case is considered in which the mixing section 148 is not provided but alternately the length of the very fine flow path 143 is made sufficiently long (for example, several hundreds of mm) and the analyte liquid Lq is stored in the volume of the very fine flow path 143. In this form, by making the same amount of analyte liquid Lq flow reciprocatingly as in the example in FIGS. 5a through 5d, it is possible to make the same amount of analyte liquid Lq pass over the top surface of the reaction field 14A. However, inside the very fine flow path 143, since the liquid flowing inside is fed in the laminar flow state, if the analyte liquid Lq inside the very fine flow path 143 is merely made to flow forward and backward, the laminar flow state of the analyte liquid Lq is maintained, no replacement is carried out, the same part of the analyte liquid Lq will always be contacting the reaction field 14A, and as a result, a concentration gradient will be generated, and only a part of the analyte liquid Lq will be contributing to the reaction in the reaction field 14A.

In contrast with that, in the preferred embodiments of the present invention shown in FIG. 1, FIGS. 5a through 5d, or the like, in which a mixing section 148 is provided, since the analyte liquid Lq stored temporarily in the mixing section 148 is mixed inside that mixing section, the concentration gradient is removed, and the analyte liquid Lq contacting the reaction field and contributing to the reaction is always renewed. In other words, in the step of repeatedly carrying out liquid feeding, most of the analyte liquid Lq will contribute to the reaction in the reaction field 14A (details are explained later). Effects of mixing can also be expected similarly in the pipette 150 that functions as an analyte liquid storage section.

Figure 5C:
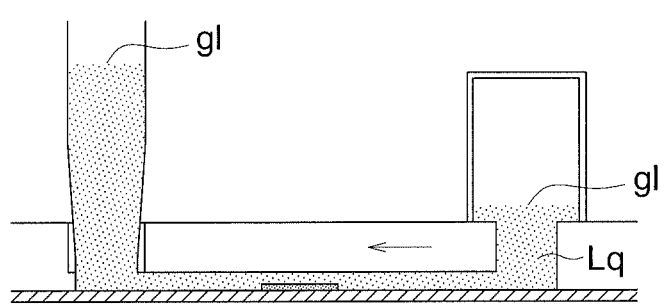

FIG. 5c is a schematic diagram showing the state immediately after the second liquid feeding step in which sucking in was carried out. The liquid feeding amount m4 in this second liquid feeding step (step S12) is taken as 185 μl, which is smaller than the injected amount m1 of liquid from which the volume m2 is subtracted. Because of this, the amount remaining in the mixing section will be 5 μl (not zero), and the front and rear gas-liquid interfaces gl can continue to be at positions higher than the very fine liquid path 143.

In the third liquid feeding step (step S13), the ejecting shown in FIG. 5b and the sucking in shown in FIG. 5c are carried out alternatingly. This is repeated until a prescribed number of repetitions have been completed (step S14: Yes). By doing this, it is possible to make a sufficient amount of the analyte liquid Lq pass over the top surface of the reaction field 14A and react. Further, since the flow rate during liquid feeding is, for example, 1000 μl/min, and since the prescribed number of times is from several tens to several hundreds of times, the time required is from several minutes to about 60 minutes.

Figure 5D:
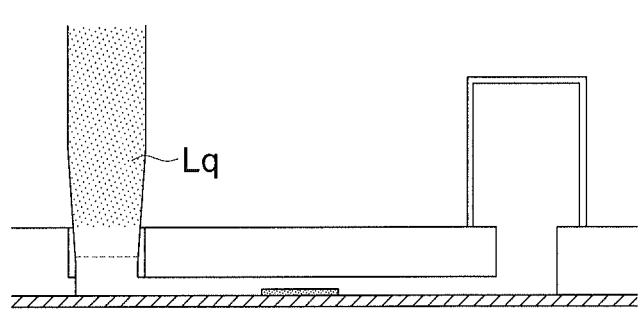

When the prescribed number of times has been completed, next, the fourth liquid feeding step (step S15) of expelling the analyte liquid Lq from the reaction field 14A is carried out. In the fourth liquid feeding step (from FIGS. 5b through 5d), the liquid feeding amount m5 is taken as 205 µl. By doing this, the entire analyte liquid Lq inside the microchip can be recovered into the pipette 150. Further, from the third liquid feeding step to the fourth liquid feeding step, the front gas-liquid interface gl in the direction of liquid feeding does not pass over the reaction field. FIG. 5d is a diagram showing that state. After recovering, the pipette 150 is pulled out from the connection section 145 (step S16) to end the operations (Return).

Further, in the third liquid feeding step of repeating ejecting and sucking in, the liquid feeding amount m4 is taken as 185 µl which is smaller than the injected amount m1 from which the volume m2 is subtracted. By making the liquid feeding amount m4 smaller than the amount of liquid obtained by subtracting the volume m2 from the injected amount m1, the front and rear gas-liquid interfaces gl can continue to be positioned above the height of the inside surface of the top wall of the very fine flow path 143 in the reaction field 14A during the third liquid feeding step. The effect is described later.

Further, in the preferred embodiment shown in FIGS. 5a through 5d, in the fourth liquid feeding step which is the last step, although the analyte liquid Lq is being recovered into the pipette 150 by finally sucking in, it is also possible to recover the analyte liquid Lq by finally ejecting into the mixing section 148. In that case, the liquid feeding amount m5 during the final ejection is taken as 205 µl.

In step S2, a cleaning liquid is fed. The step of liquid feeding is carried out similar to the subroutine shown in FIG. 4. By feeding the cleaning liquid, the analyte liquid remaining in the reaction field 14A is removed.

In step S3 of FIG. 3, since the antigen included in the analyte liquid Lq in the reaction field 14A according to step S1 specifically reacts with and is captured by the primary antibody fixed to the reaction field 14A, a secondary antibody (with fluorescent labeling) that specifically reacts with that antigen is fed by liquid feeding. The step of liquid feeding is carried out similar to the subroutine shown in FIG. 4. Further, in the example shown in FIG. 3, although an example was shown in which the analyte liquid and the secondary antibody were fed separately, it is not necessary to be restricted to this, and it is also possible to supply from the pipette 150 a liquid in which the antigen and the secondary antibody have been reacted beforehand. In this case, it is possible to omit step S3.

In step S4, a cleaning liquid is fed. The step of liquid feeding is carried out similar to the subroutine shown in FIG. 4. By feeding the cleaning liquid, the fluorescent labeling that remains in the reaction field 14A and is not contributing to the reaction is removed.

In step S5, in the state in which a buffer liquid is introduced, by making the exciting light b1 incident on the thin metal film 102 at the resonance angle θ1 that has been described earlier, density waves (surface plasmons) are generated in the thin metal film. Next, the fluorescent labeling captured in the reaction field 14A is excited by these density waves, and from this, by receiving the fluorescence light b3 in the light receiving section 120, very small amounts and/or extremely low concentrations of the analyte (the target antigen) are detected.

The above is the control flow of analyte detection. Here, the effect of the gas-liquid interface gl in the liquid feeding step of repetitions continuing to be positioned higher than the height of the inside surface of the top wall of the very fine flow path 143 is described. In the present preferred embodiment, since the very fine flow path 143 is extending in the horizontal direction, since the "height of the inside surface of the top wall of the very fine flow path 143 in the reaction field 14A" and the "height of the inside surface of the top wall of the very fine flow path 143 outside the reaction field 14A" are the same, hereinafter the "height of the inside surface of the top wall of the very fine flow path 143 in the reaction field 14A" is also referred to merely as "the horizontal plane passing through the very fine flow path 143".

[Effect of Positioning the Gas-Liquid Interface gl Higher than the Horizontal Plane Passing through the Very Fine Flow Path 143]

Figure 6A:
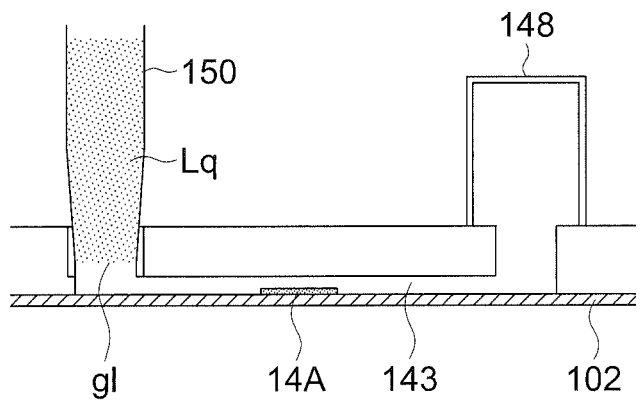
FIGS. 6a through 6d are schematic diagrams for explaining the flow of liquid feeding in a comparison example.
Figure 6B:
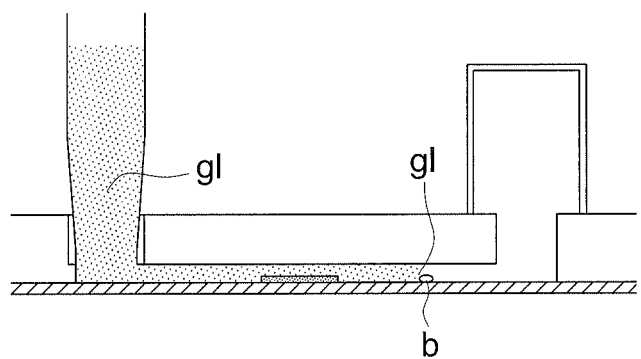
Figure 6C:
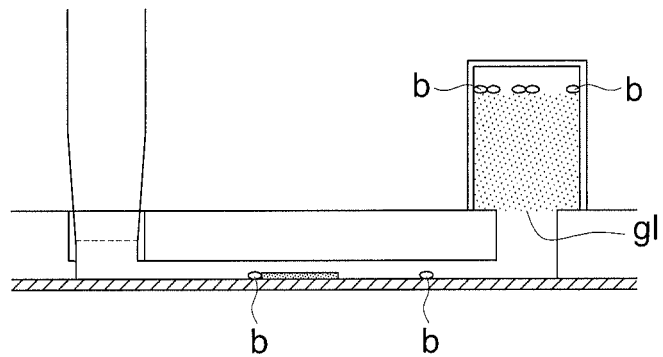
Figure 6D:
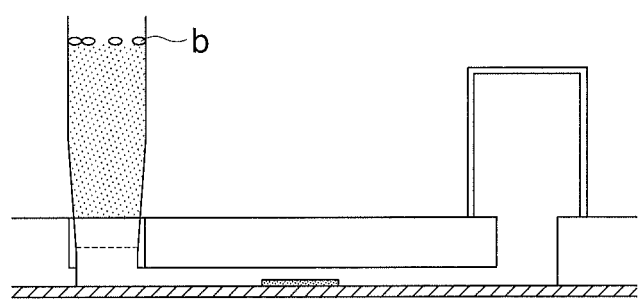

FIGS. 6a through 6d are schematic diagrams for explaining the flow of liquid feeding in a comparison example. In these figures, the gas-liquid interface gl during the liquid feeding step of repeating ejecting and sucking in correspondence to the third liquid feeding step of the present patent application are not positioned higher than the horizontal plane passing through the very fine flow path 143 but are passed through the inside of the very fine flow path 143 (particularly, the very fine flow path 143 at the reaction field 14A). FIG. 6a shows the initial state in which the pipette 150 is inserted in the microchip 12. FIG. 6b is a schematic diagram showing the flow of liquid feeding during the ejecting and sucking in during repetitions. FIG. 6c is a schematic diagram showing the state immediately after ejecting, and FIG. 6d is a schematic diagram showing the state immediately after sucking in corresponding to the fourth liquid feeding step. In the comparison example shown in this figure, liquid feeding is being made so that the gas-liquid interface gl passes through the reaction field 14A of the very fine flow path 143.

Sine the walls of the very fine flow path 143 become hydrophilic due to the proteins included in the analyte liquid Lq, in the different steps of liquid feeding, the analyte liquid Lq overtakes air and hence air bubbles b are generated. Although their effect is small when the number of liquid feedings is small, when repetitions are made a plurality of times, air bubbles b are generated in large numbers and their effect cannot be ignored. When air bubbles b are generated, the air bubbles b themselves become dampers causing deterioration of the responsivity of liquid feeding, or the flow of liquid becomes poor near the connection section 145 of connecting the pipette 150 to the flow path due to the effect of air bubbles b. Further, if the air bubbles b cover the reaction field 14A, since that part does not contact the analyte liquid Lq, reaction does not occur and the analyte is not captured. Because of this phenomenon, the amount of reaction of the analyte liquid Lq in the reaction field decreases, and as a result, it will not be possible to detect the analyte with good accuracy.

In the comparison example, air bubbles b are generated because liquid feeding is being done in this manner so that the gas-liquid interface gl passes the reaction field 14A in the very fine flow path 143. In particular, when ejecting and sucking in are repeated and the to and fro flows are repeated a plurality of times, the number of times that the gas-liquid interface gl passes over the reaction field increases, and along with that the quantity of air bubbles b increases, and detection of the analyte with good accuracy cannot be made due to the effect of these air bubbles b. On the contrary, in the preferred embodiments shown in FIGS. 5a through 5d or the like, in each liquid feeding step during repetitions, since the air-liquid interface gl maintains a position higher than the horizontal plane passing through the very fine flow path 143 and does not pass the reaction field 14A, air bubbles b are not generated in these liquid feeding steps.

Further, although the gas-liquid interface is passed through the very fine flow path 143 during the first ejecting (the first liquid feeding step) of conveying the analyte liquid Lq from the pipette 150 to the very fine flow path 143, since this is only once and the amount of air bubbles b generated is not much and since even if air bubbles b are generated they are discharged to the mixing section 148. Further, since the mixing section 148 is present at a higher position than the very fine flow path 143, the air bubbles b generated during the first ejecting step and discharged to the mixing section 148 remain in the top part (gas-liquid interface gl) of the mixing section 148 during the steps of repeated liquid feeding, and do not affect the reactions in the reaction field 14A.

In this manner, in the present preferred embodiment, by making the gas-liquid interfaces at the two ends of the analyte liquid in the different liquid feeding steps positioned higher than the horizontal plane pass through said very fine flow path, it becomes possible to prevent the effects of air bubbles, and as a result, it becomes possible to detect with good accuracy even with a small amount of the sample,

[Comparison of the Amount of Analyte Liquid Contributing to the Reaction with the Comparison Example]

Here, a comparison study is made with the comparison example regarding the amount of analyte liquid contributing to the reaction. In the comparison example shown in FIGS. 6a through 6d, during the reciprocating liquid feeding step, all (the entire amount) of the analyte liquid Lq passes the reaction field 14A. On the other hand, in the present preferred embodiment shown in FIGS. 5a through 5d or the like, a part (a part of the amount) of the analyte liquid Lq does not pass the reaction field 14A in each of the liquid feeding steps from the first liquid feeding step to the fourth liquid feeding step. In the state shown in FIG. 5b, the analyte liquid Lq on the downstream side (to the left) of the reaction field 14A, and the analyte liquid Lq on the upstream side (to the right) of the reaction field 14A in the state shown in FIG. 5c do not pass the reaction field 14A. Certainly, although a part of the analyte liquid Lq does not pass the reaction field in each of the liquid feeding steps and does not contribute to the reaction, since the liquid is mixed in the pipette 150 or in the mixing section 148, the effect thereof becomes small.

Figure 7A:
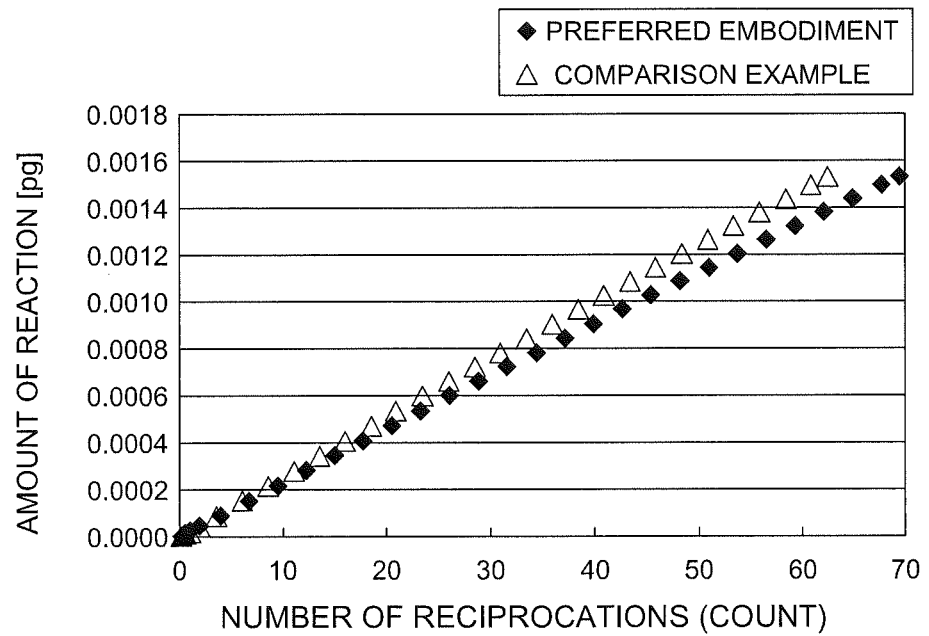
FIGS. 7a and 7b show the results of calculating the amount of reaction by simulation.
Figure 7B:
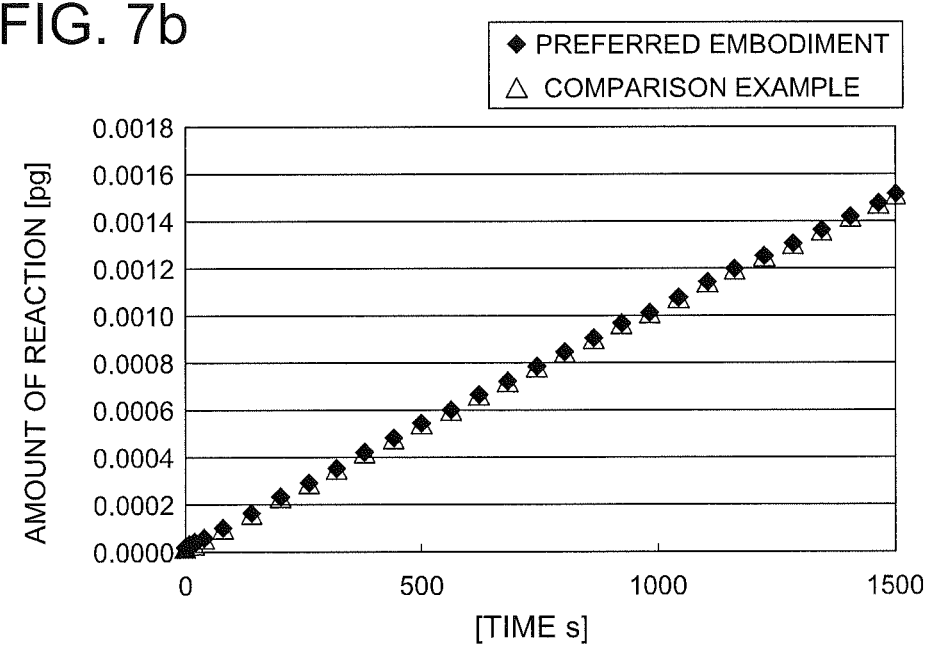

In the following, we estimated the extent of the effect. Table 1 shows the values of the rate of efficient use of the residual solution that does not pass the reaction field 14A calculated from the extent of mixing and the number of reciprocations. The graph of FIGS. 7a and 7b are examples of the calculated results of the effect of a very small change in the amount of sample (increase in the amount of sample that does not contribute to the reaction) on the amount of reaction.

TABLE 1

| Number of reciprocations N | The rate at which the liquid remaining in the storage section at the (N − 1)th reciprocation is being mixed and used effectively at the Nth reciprocation and beyond (number of reciprocations required) | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | ... 70 |
| 1 | 30.0 | | | | | | | | | | | | | | | | |
| 2 | 72.0 | 30.0 | | | | | | | | | | | | | | | |
| 3 | 88.8 | 72.0 | 30.0 | | | | | | | | | | | | | | |
| 4 | 95.5 | 88.8 | 72.0 | 30.0 | | | | | | | | | | | | | |
| 5 | 98.2 | 95.5 | 88.8 | 72.0 | 30.0 | | | | | | | | | | | | |
| 6 | 99.3 | 98.2 | 95.5 | 88.8 | 72.0 | 30.0 | | | | | | | | | | | |
| 7 | 99.7 | 99.3 | 98.2 | 95.5 | 88.8 | 72.0 | 30.0 | | | | | | | | | | |
| 8 | 99.9 | 99.7 | 99.3 | 98.2 | 95.5 | 88.8 | 72.0 | 30.0 | | | | | | | | | |
| 9 | 100.0 | 99.9 | 99.7 | 99.3 | 98.2 | 95.5 | 88.8 | 72.0 | 30.0 | | | | | | | | |
| 10 | 100.0 | 100.0 | 99.9 | 99.7 | 99.3 | 98.2 | 95.5 | 88.8 | 72.0 | 30.0 | | | | | | | |
| 11 | 100.0 | 100.0 | 100.0 | 99.9 | 99.7 | 99.3 | 98.2 | 95.5 | 88.8 | 72.0 | 30.0 | | | | | | |
| 12 | 100.0 | 100.0 | 100.0 | 100.0 | 99.9 | 99.7 | 99.3 | 98.2 | 95.5 | 88.8 | 72.0 | 30.0 | | | | | |
| 13 | 100.0 | 100.0 | 100.0 | 100.0 | 100.0 | 99.9 | 99.7 | 99.3 | 98.2 | 95.5 | 88.8 | 72.0 | 30.0 | | | | |
| 14 | 100.0 | 100.0 | 100.0 | 100.0 | 100.0 | 100.0 | 99.9 | 99.7 | 99.3 | 98.2 | 95.5 | 88.8 | 72.0 | 30.0 | | | |
| 15 | 100.0 | 100.0 | 100.0 | 100.0 | 100.0 | 100.0 | 100.0 | 99.9 | 99.7 | 99.3 | 98.2 | 95.5 | 88.8 | 72.0 | 30.0 | | |
| 16 | 100.0 | 100.0 | 100.0 | 100.0 | 100.0 | 100.0 | 100.0 | 100.0 | 99.9 | 99.7 | 99.3 | 98.2 | 95.5 | 88.8 | 72.0 | 30.0 | |
| . | . | . | . | . | . | . | . | . | . | . | . | . | . | . | . | . | . |
| 70 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | ... 30.0 |

Unit: %

In Table 1, for example, if the levels of mixing in the mixing section 148 and in the pipette 150 are respectively 60%, in the first reciprocation, since the passage through the storage section (the mixing section 148 or the pipette 150) is only once, 40% of the residual solution in the mixing section 148 will be in the state in which it is not used for the reactions. Further, at that time, since mixing has not yet been done in the pipette 150, in regard to the reaction field 14A, 100% of the residual solution will be in the state in which it is not used for the reactions. If the levels of mixing at these two ends are averaged, 70% of the residual solution at the two ends will not be used for the reactions. In other words, the rate of effective use in this state will be 30%.

However, since even the residual solution with an effective use ratio of 30% in this first reciprocation is mixed again at the two ends, the effective rate becomes 16% (40% to the power of 2) at the mixing section 148, and 40% (40% to the power of 1) at the pipette 150 and when the mixing levels at the two ends is averaged, 28% of the residual solution at the two ends has not been used in the reactions. In other words, in this state, the effective usage rate is 72%.

In this manner, since even the residual solution generated at the first reciprocation gradually gets used in the reactions the rate of effective use increases as the number reciprocations increases to the second and third reciprocations, and after nine or more reciprocations, the part of the residual solution during the first reciprocation does not lead to the reduction in the amount of sample.

Similarly, although residual solutions are generated at the respective reciprocations, by reciprocating about nine times in this manner, since all the residual solution can be made to take part in the reactions, in actuality only the part of the last ninth reciprocation leads to reduction in the amount of reaction, and the amount of sample decreases by that amount. (If 70 reciprocations are made, only 30% of the residual solution generated at the 70th reciprocation will be used for the reactions.)

For example, with a sample quantity of 200 µl when reciprocations in which 5 µl remains at each of the two ends as residual solution are made 70 times, since the average mixing ratio of the entire residual solution becomes 96.74% (the average of all values in the table), under the assumption that the mixing level is 100% (the effect of concentration gradient in the proximity of the reaction field 14A due to laminar flow is assumed to be negligible), compared to the comparison example in which the entire sample is reciprocated by passed over the reaction field 14A, the amount of sample decreases by only a very small amount of 0.326 µl. In this manner, the effect on reduction in the amount of reaction is extremely low.

The graphs of FIGS. 7a and 7b show the results of calculation of the amount of reaction by simulation. The amount of reaction is shown against the liquid feeding time. FIG. 7a shows the amount of reaction (the amount of antigen captured in the reaction field) against the number of reciprocations, and FIG. 7b shows the same data as of FIG. 7a but with the horizontal axis changed to the liquid feeding time.

(Conditions):

| | |
|---|---|
| Liquid feeding velocity: | 1000 µl/min. |
| Liquid feeding time: | 1500 sec. |
| Amount of sample: | 200 µl |
| Amount of liquid feeding during one reciprocation (one direction): | Preferred embodiment 1: 185 µl, comparison example: 200 µl |

Preferred Embodiment

As is shown in FIGS. 5a through 5d, the gas-liquid interface gl is not passed inside the very fine flow path 143.

Comparison Example

As is shown in FIGS. 6a through 6d, the gas-liquid interface gl is passed inside the very fine flow path 143. However, it is assumed that air bubbles b are not generated due to this passage and that liquid feeding can be made without any problem having occurred.

Both FIG. 7a and FIG. 7b are for the same liquid feeding time (the amount of liquid feeding is the same), in the graph of FIG. 7a of the amount of reaction for the number of reciprocations, although the amount of reaction is higher in the comparison example than the preferred embodiment due to the difference in the amount of liquid feeding during the first reciprocation, as is shown in FIG. 7b, in the comparison for the same liquid feeding time (same amount of liquid feeding), there is almost no reduction in the amount of reaction in the preferred embodiment compared to the comparison example. The rate of reduction in the preferred embodiment compared to the comparison example is less than 0.015%, which can be said to be of a lever that is not a problem.

Second Preferred Embodiment

A liquid feeding system for a microchip and an analyte detection device using this liquid feeding system for a microchip according to a second preferred embodiment can accumulate the analyte liquid certainly within the detection region even if the quantity of the analyte liquid is small, and because of this, it is possible to retain the desired analyte within the detection region and to detect the analyte with a high accuracy.

Figure 8:
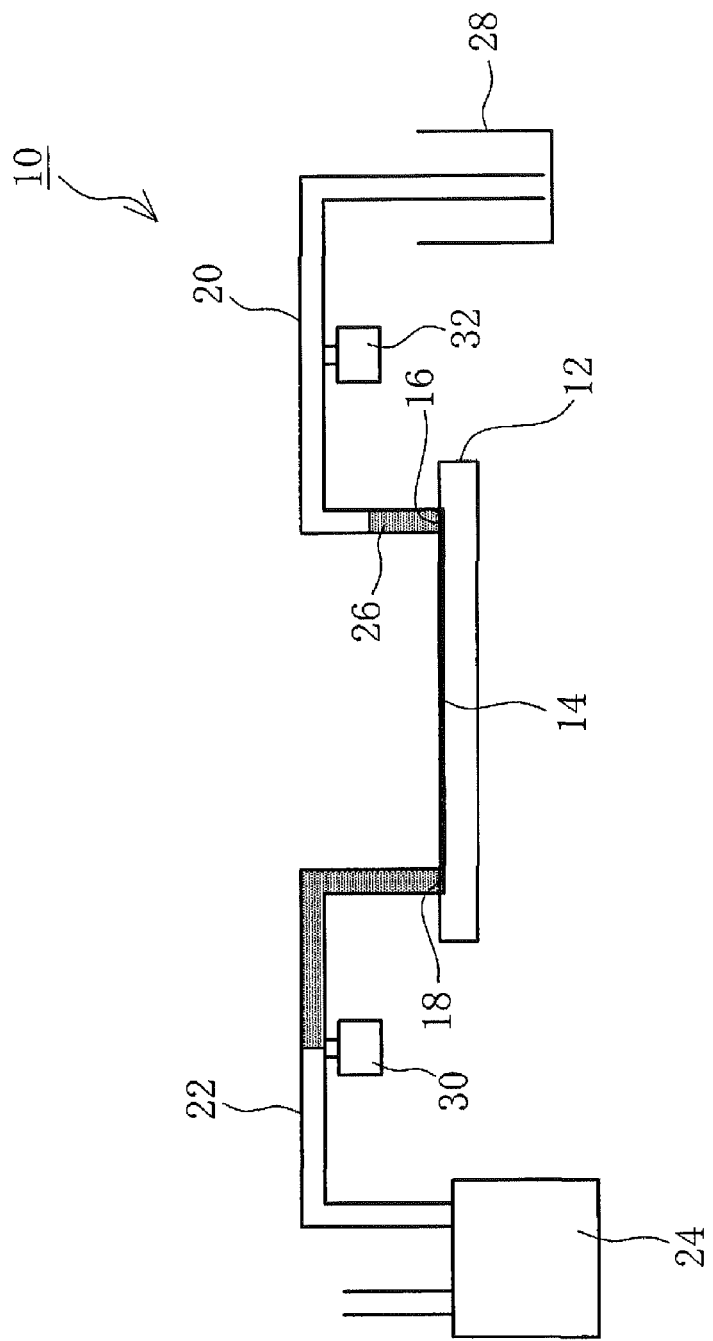
FIG. 8 is a schematic diagram for explaining the reciprocating type liquid feeding system for a microchip according to a second preferred embodiment.
Figure 9A:
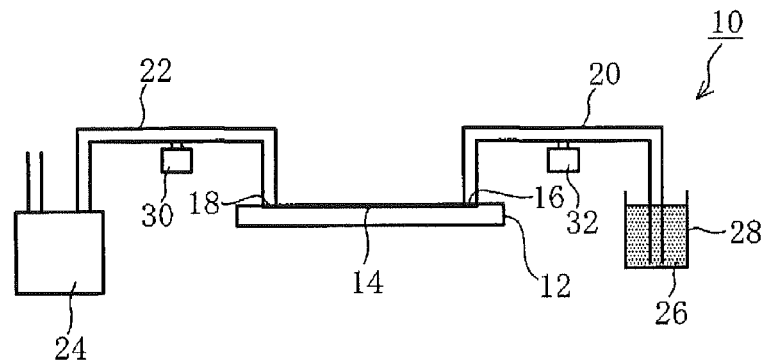
FIG. 9a through 9d is a schematic diagram for explaining a reciprocating type liquid feeding system for a microchip according to a second preferred embodiment.
Figure 9B:
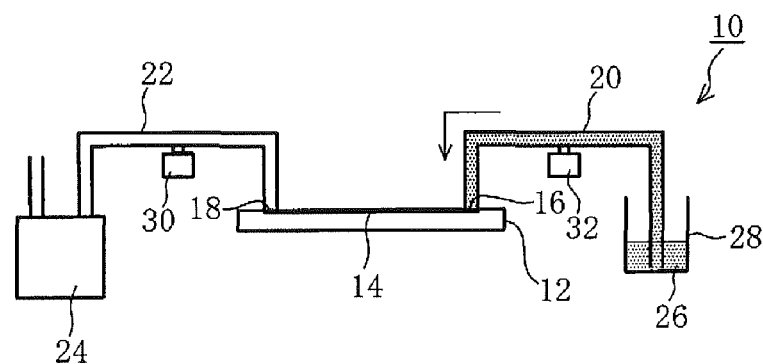
Figure 9C:
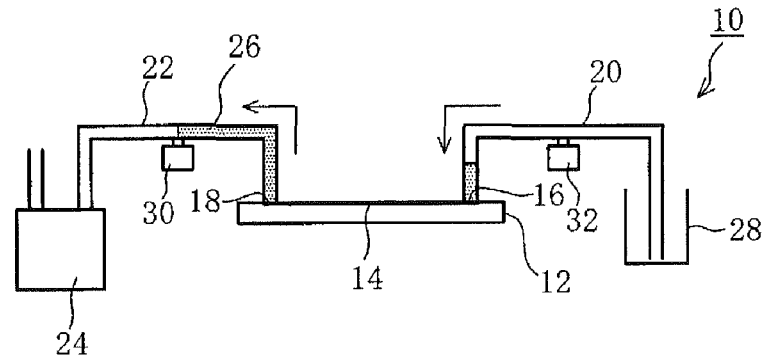
Figure 9D:
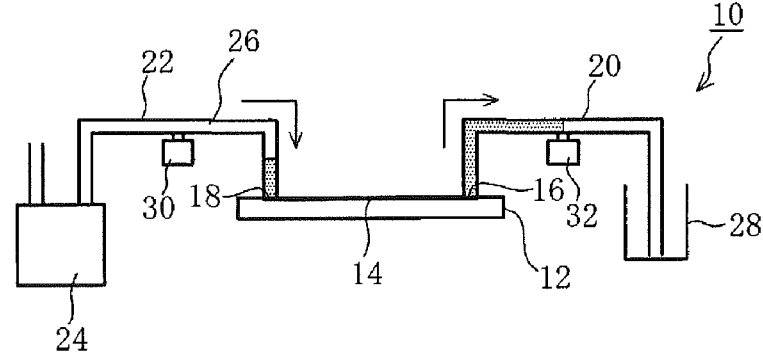
Figure 10:
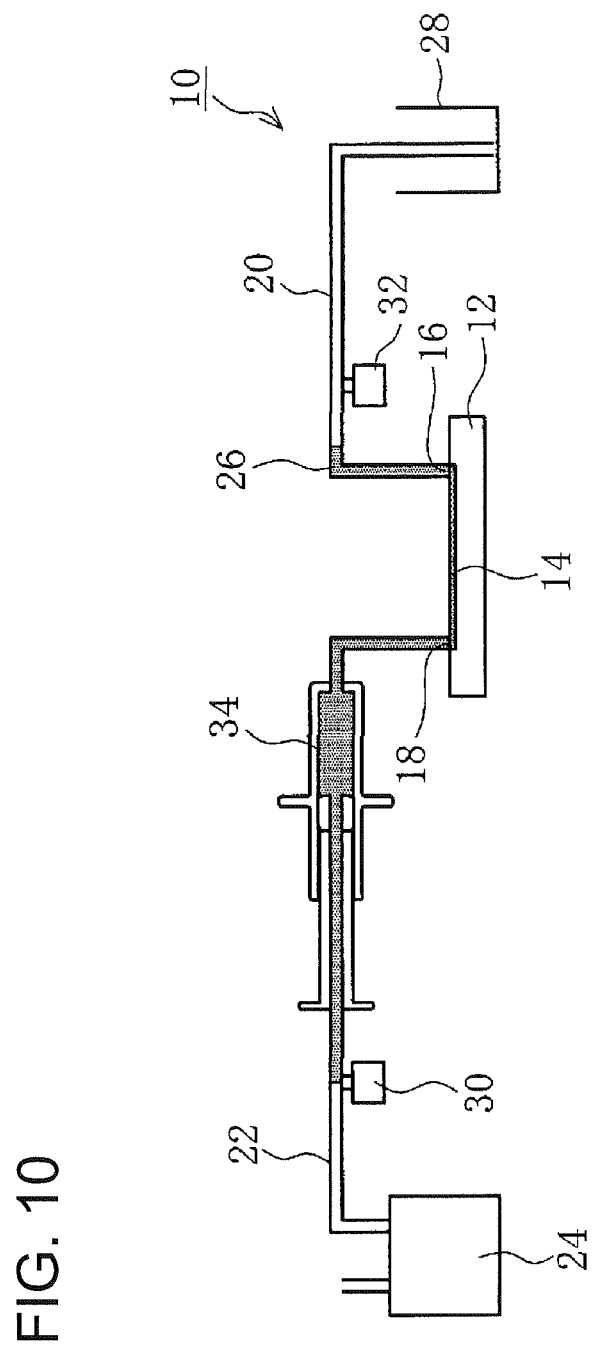
FIG. 10 is a schematic diagram for explaining the variable volume section in a reciprocating type liquid feeding system for a microchip according to the second preferred embodiment.
Figure 11A:
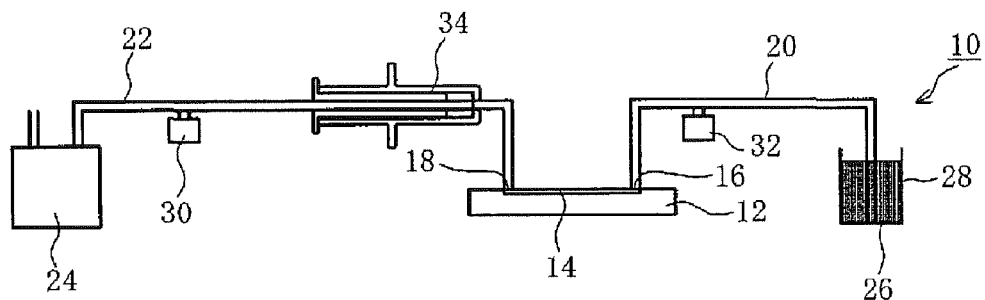
FIGS. 11a through 11d are schematic diagrams for explaining the operating states of the variable volume section.
Figure 11B:
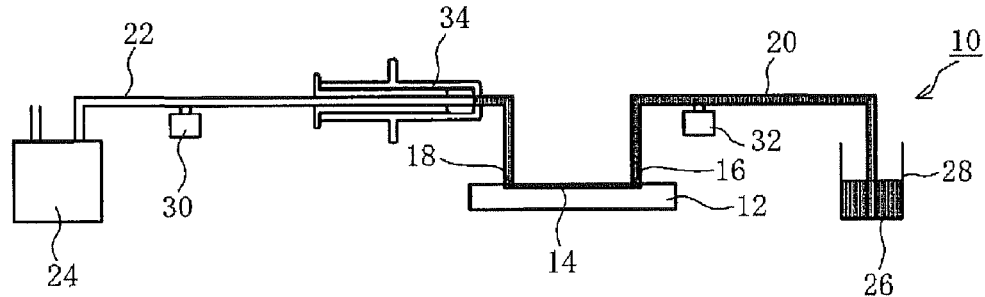
Figure 11C:
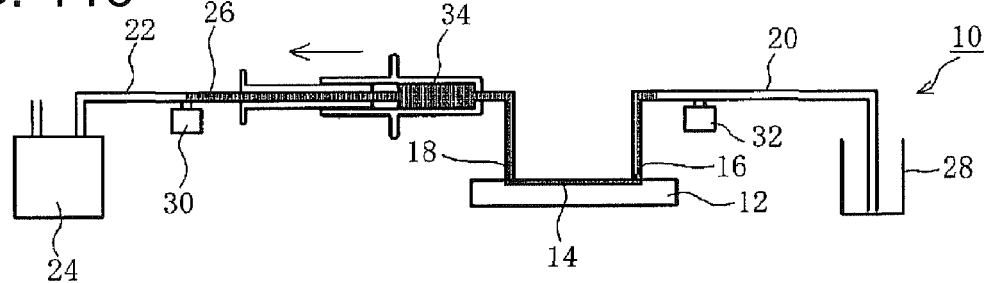
Figure 11D:
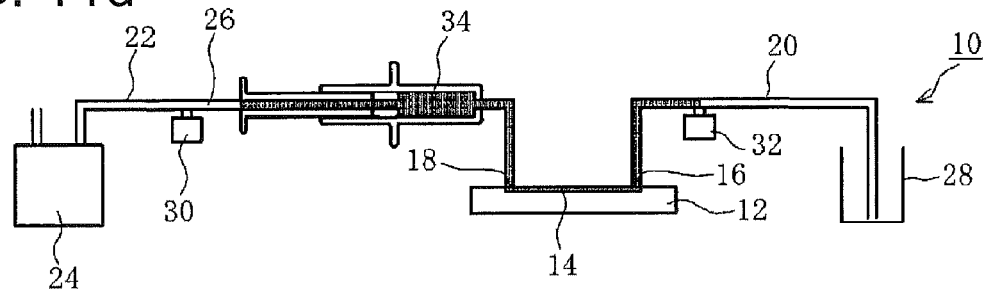
Figure 12A:
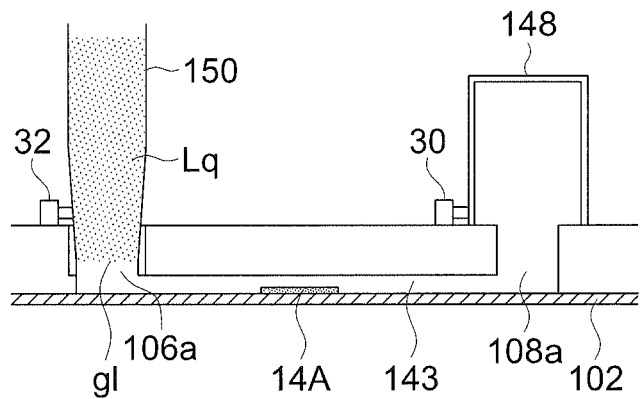
FIGS. 12a through 12d are schematic diagrams for explaining a reciprocating type liquid feeding system for a microchip according to a further modified example of the second preferred embodiment.
Figure 12B:
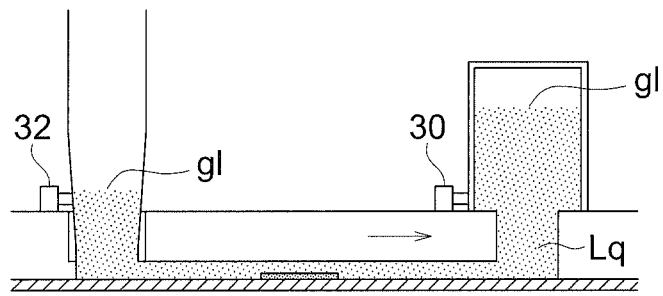
Figure 12C:
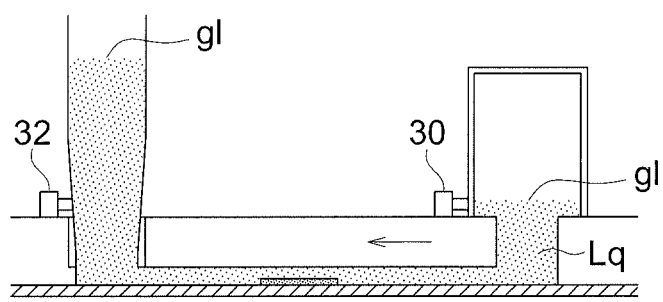
Figure 12D:
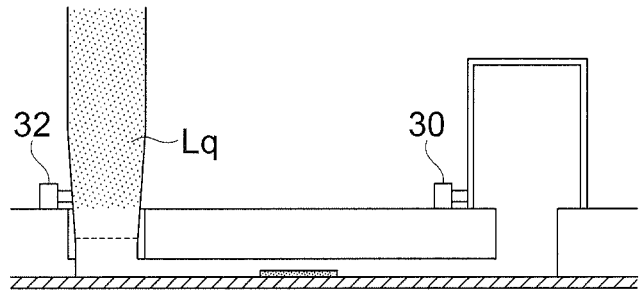

In the following, more detailed explanations are given based on the drawings. FIG. 8 is a schematic diagram for explaining the reciprocating type liquid feeding system for a microchip according to a second preferred embodiment, FIGS. 9a through 9d are schematic diagrams for explaining a reciprocating type liquid feeding system for a microchip according to a second preferred embodiment, FIG. 9a is a state diagram before the analyte liquid 26 is fed by the reciprocating liquid feeding pump, FIG. 9b is a state diagram during period in which the analyte liquid 26 is being fed by the reciprocating liquid feeding pump, FIG. 9c is a state diagram when the analyte liquid 26 is fed by the reciprocating liquid feeding pump and the first liquid position checking sensor 30 has detected the analyte liquid, and FIG. 9d is a state diagram when the liquid feeding direction of the reciprocating liquid feeding pump has been switched to the opposite direction and the second liquid position checking sensor 32 has detected the analyte liquid, FIG. 10 is a schematic diagram for explaining the variable volume section 34 in a reciprocating type liquid feeding system for a microchip according to the second preferred embodiment, FIGS. 11a through 11d are schematic diagrams for explaining the operating states of the variable volume section 34, FIG. 11a is a state diagram before actuating the variable volume section 34, FIG. 11b is a state diagram immediately before actuating the variable volume section 34, FIG. 11c is a state diagram when the variable volume section 34 is actuated and also the first liquid position checking sensor has detected the analyte liquid, and FIG. 11d is a state diagram when the liquid feeding direction of the reciprocating liquid feeding pump has been switched to the opposite direction and the second liquid position checking sensor has detected the analyte liquid.

As is shown in FIG. 8, in the liquid feeding system 10 of the reciprocating type for a microchip according to a second preferred embodiment, firstly in the reaction field 14 of the microchip 12 are provided, an inlet hole 16 which is an inlet for passing an analyte liquid 26, and an outlet hole 18 which is an outlet for the analyte liquid 26 which was passed from this inlet hole 16.

Next, to these inlet holes 16 and outlet hole 18 is connected respectively one end section each of the inlet side passage path 20 and outlet side passage path 22. In addition, to the other end section of the inlet side passage path 20 is connected an analyte liquid container vessel 28 that accommodates the analyte liquid 26, and to the other end section (corresponding to "the side opposite the flow path of primary storage section") of the outlet side passage path 22 is provided by connecting a reciprocating liquid feeding pump 24.

In the second preferred embodiment, the analyte liquid container vessel 28, or the analyte liquid container vessel 28 and the inlet side passage path 20 function as an "analyte liquid storage section", and the outlet side passage path 22 functions as a "primary storage section".

Further, in the middle of the outlet side passage path 22 is provided a first liquid position checking sensor 30, and in addition in the middle of the inlet side passage path 20 is provided a second liquid position checking sensor 32. A liquid feeding system 10 for a microchip configured in this manner, firstly as is shown in FIG. 9a, before actuating the liquid feeding system 10 for a microchip, first a prescribed analyte liquid 26 is stored to begin with inside the analyte liquid container vessel 28.

Next, by actuating the reciprocating liquid feeding pump 24 in this state, as is shown in FIG. 9b, a prescribed amount of the analyte liquid in the analyte liquid container vessel 28 is fed from the inlet hole 16 of the reaction field 14 in the direction towards the outlet hole 18 (first liquid feeding step).

When the liquid feeding is continued further, as is shown in FIG. 9c, although the analyte liquid 26 passes through the outlet side passage path 22 and flows towards the reciprocating liquid feeding pump 24, but at this time, when the first liquid position checking sensor 30 provided in the middle of the outlet side passage path 22 detects the analyte liquid 26, the direction of liquid feeding of the reciprocating liquid feeding pump 24 is reversed (from ejecting to sucking in), and as is shown in FIG. 9d, this time the liquid feeding is made in the direction from the outlet hole 18 towards the inlet hole 16 (second liquid feeding step). At this time, the rear part of the gas-liquid interface of the analyte liquid is inside the inlet side passage flow path 20 and is before the reaction field 14. In other words, the rear gas-liquid interface of the analyte liquid 26 does not pass the reaction field 14.

Next, when the analyte liquid 26 fed in the direction from the outlet hole 18 towards the inlet hole 16, this time flows into the inlet side passage path 20, the second liquid position checking sensor 32 provided in the middle of the inlet side passage path 20 detects the analyte liquid 26, this detection information is conveyed to the reciprocating liquid feeding pump 24, and the direction of liquid feeding of the reciprocating liquid feeding pump 24 is again reversed.

By repeating this changing of the liquid feeding direction (third liquid feeding step), it is possible to make the analyte liquid 26 carry out certainly a reciprocating movement inside the reaction field 14. At this time, it is possible to carry out reciprocating movement of the analyte liquid 26 if the amount of feeding of the analyte liquid 26 (a prescribed amount fed from the analyte liquid container vessel 28) is an amount that is equal to or more than an amount that fills the reaction field 14, and also, larger than the bigger of the volume of the outlet side passage path 22 from the reaction field 14 to the first liquid position checking sensor 30 and the volume of the inlet side passage path 20 up to the second liquid position checking sensor 32, but smaller than an amount that fills the entire passage path with the analyte liquid 26 from the first liquid position checking sensor 30 to the second liquid position checking sensor 32 including the reaction field 14. By making the amount of analyte liquid equal to such an amount, in the third liquid feeding step, since the front and rear gas-liquid interfaces of the analyte liquid 26 do not pass the reaction field 14, without generating air bubbles, there is no generation of problems such as the responsivity of the liquid flow getting deteriorated due to the generated air bubbles, nor of reducing the amount of reaction of the analyte in the reaction field 14.

Because of this, by making the first liquid position checking sensor 30 come closer to the outlet hole 18 and the second liquid position checking sensor 32 come closer to the inlet hole 16, it is possible to make small the amount of liquid feeding necessary for reciprocating liquid feeding.

Further, if the first liquid position checking sensor 30 and the second liquid position checking sensor 32 can detect whether or not the analyte liquid 26 is present at prescribed positions, the sensors can be any sensors, and are not particularly restricted.

In the above explanations, although the configuration was one in which the direction of liquid feeding was switched at the time that the analyte liquid 26 was detected by the first liquid position checking sensor 30 and at the time that the analyte liquid 26 was detected by the second liquid position checking sensor 32, it is also possible to configure so that control is carried out so as to switch the direction of liquid feeding during liquid feeding at the time that the analyte liquid 26 that was being detected by the second liquid position checking sensor 32 is no longer detected and at the time that the analyte liquid 26 that was being detected by the second liquid position checking sensor 32 is no longer detected.

Further, in the liquid feeding system 10 for a microchip according to the present invention, it is also possible to use any method for carrying out liquid feeding of the analyte liquid 26 by the reciprocating liquid feeding pump 24, and for example, while it is possible to use a driving fluid such as air, or oil, or the like, among them, using air is preferable from the point of view of preventing contamination, and certainly preventing non-specific adsorption.

Further, when using air, by making the volume between the reciprocating liquid feeding pump 24 and the analyte liquid inside the outlet side passage path 22 as small as possible, that is, by making the amount of air as small as possible, the switching of the direction of liquid feeding by the reciprocating liquid feeding pump can be carried out smoothly.

Further, while for the reciprocating liquid feeding pump 24 it is possible to use any type of pump such as, for example, a Perista pump, a syringe pump, or the like, among them, a Perista pump is preferable because it will not be necessary to take in air into the pump.

In addition, the inlet side passage path 20 and the outlet side passage path 22 can be passage paths made of any material, and although not particularly restricted, using transparent plastic tubes made of a hard material that is difficult to be deformed by air pressure is preferable from the point of obtaining reciprocating accuracy, from the point of making easy the detection of the analyte liquid 26 by the sensors, and from the point of being able to view the material inside.

Further, in the liquid feeding system 10 for a microchip shown in FIGS. 9a through 9d, although the configuration is one in which only an amount of the analyte liquid necessary for carrying out reciprocating liquid feeding to the reaction field 14 is present inside because of detection of the analyte liquid 26 by the sensors, it is possible to inject analyte liquid 26 for several times if the analyte liquid containing vessel 28 is one with a large capacity.

In this case, by providing a liquid amount detecting sensor (not shown in the figure) in the liquid feeding system 10 for a microchip, and by detaching the analyte liquid containing vessel 28 from the inlet side passage path 20 when the liquid amount detecting sensor (not shown in the figure) detects that the reciprocating liquid feeding pump 24 has fed a predetermined prescribed amount of analyte liquid 26, it is possible to use certainly only a prescribed amount of the analyte liquid 26.

Further, at the time of detaching the analyte liquid containing vessel 28 from the inlet side passage path 20, it can be done either manually or automatically, and for example, when carrying this out automatically, when the liquid amount detecting sensor (not shown in the figure) is actuated, it is possible to cause the analyte liquid containing vessel 28 to move down so that the analyte liquid 26 is separated from the end section of the inlet side passage path 20.

As in the second preferred embodiment, if a first liquid position checking sensor and a second liquid position checking sensor are provided, since it is possible to detect constantly the position of the analyte liquid, it is possible to carry out reciprocating movement in the state in which the analyte liquid is accumulated inside the detection region, and because of this, it is possible to retain the analyte within the detection region and to detect the analyte with a good accuracy.

Further, in the passage path on the side which is not connected to the reciprocating liquid feeding pump 24, if a switching valve is provided for opening to atmosphere at a position separated from the reaction field 14 than the liquid position checking sensors placed inside that passage path, and, when the liquid amount detection sensor (not shown in the figure) is actuated, it is also possible to make the connection with the analyte liquid containing vessel 28 switched to the open to atmosphere state.

If a liquid amount detecting sensor is provided, it is also possible to use a large quantity of the analyte liquid by dividing it into several times, and it is possible to reduce the time required for detecting the analyte. Therefore, it is possible to detect the analyte a plurality of times, and to increase the accuracy of analyte detection.

In addition, the reciprocating liquid feeding pump 24 has been provided by connecting to the other end of the outlet side passage path 22 (corresponds to "the side opposite to that of the flow path of the primary storage section"). In this case, if the length of the outlet side passage path is set so that the distance between the first liquid position checking sensor and the reciprocating liquid feeding pump 24 becomes short, since the amount of air in this space becomes smaller, the responsivity of the reciprocating liquid feeding pump becomes good.

Modified Example of the Second Preferred Embodiment

Further, depending on the type of analyte, there are cases when a larger than normal amount of analyte liquid 26 is unavoidably necessary, and in this case, as is shown in FIG. 10, it is preferable that, in the middle of one of the inlet side passage path 20 and the outlet side passage path 22 (in the middle of the outlet side passage path in FIG. 10), a variable volume section 34 is provided that has a larger diameter than the diameter of the passage path and that can store a large amount of the analyte liquid 26.

Such a variable volume section 34, as is shown in FIG. 11*a*, before the liquid feeding system 10 for a microchip is actuated, is set so that the volume of the variable volume section 34 is at its lowest. Next, the liquid feeding system 10 for a microchip is actuated, and as is shown in FIG. 11*b*, the volume of the variable volume section is maintained at its lowest until the analyte liquid 26 is injected to fill the variable volume section 34 which is in the lowest volume state.

After that, as is shown in FIG. 11*c*, matching with the flow velocity of the analyte liquid 26, by gradually increasing the volume of the variable volume section 34, even if the amount of analyte liquid 26 becomes large, the length of the passage path becoming longer than necessary can be prevented.

Next, when the first liquid position checking sensor 30 provided in the middle of the outlet side passage path 22 detects the analyte liquid 26, the direction of liquid feeding by the reciprocating liquid feeding pump 24 is switched, and this time, as is shown in FIG. 11*d*, the analyte liquid 26 is fed in the direction from the outlet hole 18 towards the inlet hole 16, when the analyte liquid 26 is detected by the second liquid position checking sensor 32 of the inlet side passage path 20, the direction of liquid feeding by the reciprocating liquid feeding pump 24 is switched again.

Further, making the timing of increasing the volume of the variable volume section 34 later than the variable volume section 34 being filled with the analyte liquid 26 is to make sure that the amount of air in the passage path placed on the side where the variable volume section 34 has been placed is not changed between before and after the volume of the variable volume section 34 is changed.

Here, when the change in the volume of the variable volume section 34 is carried out matching with the amount of movement of the analyte liquid 26 due to the drive by the reciprocating liquid feeding pump 24, it is possible to carry this out manually or automatically, and is not particularly restricted. In addition, it is preferable to make the minimum volume of the variable volume section 34 equal to zero as is shown in FIG. 11*b*.

Preferably, a stored volume varying mechanism (not shown in the figure) is provided to the variable volume section 34, thereby making the volume of the variable volume section 34 change automatically matching with the liquid feeding velocity of the analyte liquid 26.

As in the modified example of the second preferred embodiment, if a variable volume section has been provided, for example, even when a large quantity of the analyte liquid is necessary depending on the analyte, it is not necessary to make the length of the passage of the inlet side passage path or of the outlet side passage path longer than necessary.

Because of a stored volume varying mechanism that automatically varies the volume of the variable volume section 34 matching with the liquid feeding velocity of the analyte liquid 26, for example, if the setting is made so that the volume of the variable volume section is increased after the analyte liquid is injected into the variable volume section, the amount of air in the passage path on the side in which the variable volume section is installed can be made not to change before and after the volume of the variable volume section is increased.

In this manner, the liquid feeding system 10 for a microchip according to the second preferred embodiment, by providing a first liquid position checking sensor 30 and a second liquid position checking sensor 32, not only it is possible to carry out reciprocating liquid feeding while certainly accumulating the analyte liquid 26 inside the reaction field 14 even when the analyte liquid is small, but also, by providing a variable volume section, there is no need to change the positions of the first liquid position checking sensor 30 and the second liquid position checking sensor 32, it is easily possible to adjust the amount of air inside the passage path to a fixed value, and to switch the direction of liquid feeding with a good sensitivity.

Because of this, if this liquid feeding system 10 for a microchip is used in an analyte detection device, particularly in a surface plasmon field enhanced resonance apparatus (SPR apparatus) or in a surface plasmon field enhanced fluorescence spectroscopy apparatus (SPFS apparatus) as is shown in FIG. 1, it is possible to detect with a high accuracy even with an extremely fine quantity of analyte.

Further Modified Example of the Second Preferred Embodiment

FIGS. 12*a* through 12*d* are schematic diagrams for explaining a reciprocating type liquid feeding system for a microchip according to a further modified example of the second preferred embodiment. This is a liquid feeding system for a microchip according to the first preferred embodiment shown in FIG. 1, FIGS. 5*a* through 5*d*, or the like, in which a first liquid position checking sensor 30 and a second liquid position checking sensor 32 have been provided.

In this figure, a first liquid position checking sensor 30 is provided inside the mixing section 148 and a second liquid position checking sensor 32 is provided inside the pipette 150. The settings of these sensors are such that the liquid surface is detected when the remaining liquid respectively inside the mixing section 148 and inside the pipette 150 becomes 5 μl.

The configuration is such that, in the third liquid feeding step, control is carried out so as to switch the direction of liquid feeding at the time during liquid feeding in the ejecting direction when the analyte liquid Lq that was being detected by the second liquid position checking sensor 32 is no longer detected and at the time during liquid feeding in the sucking in direction when the analyte liquid Lq that was being detected by the second liquid position checking sensor 32 is no longer detected. Because of this, since it is possible to detect constantly the position of the analyte liquid, it is possible to carry out reciprocating movement in the state in which the analyte liquid is accumulated inside the detection region, and because of this, it is possible to retain the analyte within the detection region and to detect the analyte with a good accuracy.

In the above, although some preferred embodiments of a liquid feeding system for a microchip according to the present invention and an analyte detection device utilizing such a system have been explained, the present invention shall not be restricted by these preferred embodiments, but various modifications are possible without deviating from the purpose of the present invention.

DESCRIPTION OF REFERENCE SYMBOLS

A Surface plasmon field enhanced fluorescence spectroscopy apparatus
- 10,10A Liquid feeding system
- 13 Control section
- b1 Excitation light
- b2 Metal thin film reflected light
- b3 Fluorescence light
- 12 Microchip
- 102 Metal thin film
- 14A, 14 Reaction field
- 86 Dielectric member
- 8A Chip structure member
- 112 Light source
- 116 Light receiving section
- 120 Light detecting section
- 122 Focusing member
- 124 Filter
- 130, 24 Reciprocating liquid feeding pump
- 12 Microchip
- 161 Fixing bracket
- 142 Substrate
- 143 Very fine flow path
- 106a, 16 Inlet hole
- 108a, 18 Outlet hole
- 145 Connection section
- 148 Mixing section
- 150 Pipette
- gl Gas-liquid interface
- Lq, 26 Analyte liquid
- b Air bubble
- 28 Analyte liquid containing vessel
- 30 First liquid position checking sensor
- 32 Second liquid position checking sensor
- 34 Variable volume section

The invention claimed is:

1. A liquid feeding system for a microchip comprising:
   a flow path having a reaction field in which is fixed an antibody that reacts specifically with an antigen in an analyte liquid;
   a pipette connected to one end side of the flow path;
   mixing chamber connected to the other end side of the flow path;
   a pump that reciprocatingly feeds the analyte liquid with respect to the reaction field by applying driving force via a gas to the analyte liquid in the pipette; and
   a processor that controls drive of the pump;
   wherein the processor is structured to drive the pump to carry out:
      a first liquid feeding step comprising feeding the analyte liquid of the pipette via the reaction field in a direction toward the mixing chamber;
      a second liquid feeding step comprising feeding the analyte liquid in a direction from the mixing chamber toward the reaction field, after the first liquid feeding step; and
      a third liquid feeding step comprising repeating the feeding of the analyte liquid in the direction from the reaction field toward the mixing chamber and the feeding of the analyte liquid in the direction from the mixing chamber toward the reaction field, after the second liquid feeding step,
   wherein the processor is structured to control the pump so that a rear gas-liquid interface of the analyte liquid in the first liquid feeding step, and a front gas-liquid interface and the rear gas-liquid interface of the analyte liquid in the second and the third liquid feeding steps do not pass beyond the reaction field, wherein the rear gas-liquid interface of the analyte liquid exists in the pipette all through the first liquid feeding step, the second liquid feeding step, and the third liquid feeding step.

2. The liquid feeding system for a microchip described in claim 1, wherein the processor carries out a fourth liquid feeding step of feeding the analyte liquid so as to be expelled from the reaction field after the third liquid feeding step, wherein the processor carries out control of the pump so that the front gas-liquid interface of the analyte liquid in the fourth liquid feeding step does not pass beyond the reaction field.

3. The liquid feeding system for a microchip described in claim 1, wherein, by the control of the processor, the rear gas-liquid interface of the analyte liquid in the first liquid feeding step and the front and rear gas-liquid interfaces in the second liquid feeding step and the third liquid feeding step continue to be positioned above a height of an inside surface of a top wall of the flow path in the reaction field.

4. The liquid feeding system for a microchip described in claim 1, comprising:
   a first liquid position checking sensor provided at a predetermined position in a middle between the reaction field and the mixing chamber or at a predetermined position in the mixing chamber, and detecting if the analyte liquid exists or not; and
   a second position checking sensor provided at a predetermined position in a middle between the reaction field and the pipette or at a predetermined position in the the pipette, and detecting if the analyte liquid exists or not;
   wherein the processor controls changing the directions of liquid feeding in the third liquid feeding step, by the detections of the first liquid position checking sensor and the second liquid position checking sensor.

5. The liquid feeding system for a microchip described in claim 4, wherein a variable volume section is provided at a middle of at least one of between the reaction field and an installation position of the first position checking sensor and between the reaction field and an installation position of the second position checking sensor.

6. The liquid feeding system for a microchip described in claim 5, wherein the variable section comprises a stored volume varying mechanism which changes a volume for storing sample liquid of the variable volume section, with matching with a liquid feeding volume of the analyte liquid by a driving of the pump.

7. The liquid feeding system for a microchip described in claim 1, comprising a liquid amount detecting sensor to detect a liquid feeding amount from the pipette.

8. The liquid feeding system for a microchip described in claim 1, wherein the pump is provided to connect to a side opposite the flow path of mixing chamber.

9. An analyte detection apparatus which is a surface plasmon field enhanced resonance apparatus (SPR apparatus) or a surface plasmon field enhanced fluorescence spectroscopy apparatus (SPFS apparatus), provided with the liquid feeding system for a microchip described in claim 1.

10. A liquid feeding method for a liquid feeding system for a microchip, the liquid feeding system comprising:
    a flow path having a reaction field in which is fixed an antibody that reacts specifically with an antigen in an analyte liquid;
    a pipette inserted into one end side of the flow path;
    a mixing chamber connected to the other end side of the flow path; and
    a pump that reciprocatingly feeds the analyte liquid with respect to the reaction field by applying driving force via a gas to the analyte liquid in the pipette, the liquid feeding method comprising:
    a first liquid feeding step comprising feeding the analyte liquid of the pipette via the reaction field in the direction of the mixing chamber;
    a second liquid feeding step comprising feeding the analyte liquid after the first liquid feeding step from the mixing chamber in the direction of the reaction field; and
    a third liquid feeding step comprising repeating, after the second liquid feeding step, the feeding of the analyte liquid in the direction from the reaction field toward the mixing chamber and the feeding of the analyte liquid in the direction from the mixing chamber toward the reaction field,
    wherein a rear gas-liquid interface of the analyte liquid in the first liquid feeding step, and a front gas-liquid interface and the rear gas-liquid interface of the analyte liquid in the second and the third liquid feeding steps do not pass beyond the reaction field, wherein the rear gas-liquid interface of the analyte liquid exists in the pipette all through the first liquid feeding step, the second liquid feeding step and the third liquid feeding step.

11. The liquid feeding system for a microchip described in claim 1, wherein the mixing chamber has a larger cross-section shape than the other end side of the flow path and comprises a fine air hole in a top part of the mixing chamber.

* * * * *